United States Patent
Frascati et al.

(10) Patent No.: US 9,684,950 B2
(45) Date of Patent: Jun. 20, 2017

(54) VISION CORRECTION THROUGH GRAPHICS PROCESSING

(71) Applicant: QUALCOMM Incorporated, San Diego, CA (US)

(72) Inventors: Christopher Paul Frascati, Oviedo, FL (US); Avinash Seetharamaiah, Chuluota, FL (US); Murat Balci, Orlando, FL (US)

(73) Assignee: QUALCOMM Incorporated, San Diego, CA (US)

( * ) Notice: Subject to any disclaimer, the term of this patent is extended or adjusted under 35 U.S.C. 154(b) by 26 days.

(21) Appl. No.: 14/574,807

(22) Filed: Dec. 18, 2014

(65) Prior Publication Data

US 2016/0180503 A1  Jun. 23, 2016

(51) Int. Cl.
*G06T 3/00* (2006.01)
*G06T 5/00* (2006.01)
*A61B 3/02* (2006.01)
*G09G 5/36* (2006.01)

(52) U.S. Cl.
CPC .............. *G06T 5/002* (2013.01); *A61B 3/02* (2013.01); *G09G 5/36* (2013.01); *G06T 2207/10004* (2013.01); *G06T 2207/20092* (2013.01); *G09G 2320/0271* (2013.01); *G09G 2320/066* (2013.01); *G09G 2320/08* (2013.01); *G09G 2354/00* (2013.01)

(58) Field of Classification Search
None
See application file for complete search history.

(56) References Cited

U.S. PATENT DOCUMENTS

| | | | |
|---|---|---|---|
| 5,436,681 A | 7/1995 | Michaels | |
| 6,982,682 B1 * | 1/2006 | Kaulgud | G06F 3/1446 345/1.1 |
| 8,212,859 B2 | 7/2012 | Tang et al. | |
| 8,353,594 B2 | 1/2013 | Lewis | |
| 8,406,562 B2 * | 3/2013 | Bassi | H04N 9/3147 348/222.1 |
| 8,488,246 B2 | 7/2013 | Border et al. | |
| 2006/0033880 A1 | 2/2006 | Korneluk | |
| 2006/0290712 A1 | 12/2006 | Hong et al. | |
| 2011/0122144 A1 | 5/2011 | Gabay | |

(Continued)

OTHER PUBLICATIONS

Pamplona et al., "Tailored Displays to Compensate for Visual Aberrations," ACM Transactions on Graphics, vol. 30, Issue 4, Jul. 2011, 12 pp.

(Continued)

*Primary Examiner* — Ryan M Gray
(74) *Attorney, Agent, or Firm* — Shumaker & Sieffert, P.A.

(57) ABSTRACT

An apparatus configured for graphics processing includes a memory configured to store graphics data, and one or more processors in communication with the memory, the one or more processors configured to output, for display, a plurality of test graphics images, receive input indicative of a perception of a user of the computing device of at least one test graphics image from the plurality of test graphics images, determine at least one parameter modification value and generate a corrected graphics image based at least in part on the at least one parameter modification value.

24 Claims, 10 Drawing Sheets

(56) References Cited

U.S. PATENT DOCUMENTS

| | | | |
|---|---|---|---|
| 2011/0248987 A1* | 10/2011 | Mitchell | G06T 15/20 345/419 |
| 2011/0310115 A1 | 12/2011 | Tine et al. | |
| 2012/0032874 A1* | 2/2012 | Mukawa | G02B 3/12 345/8 |
| 2013/0050833 A1 | 2/2013 | Lewis et al. | |
| 2013/0141697 A1 | 6/2013 | Berry et al. | |
| 2013/0258270 A1 | 10/2013 | Cazalet et al. | |
| 2013/0286053 A1 | 10/2013 | Fleck et al. | |
| 2014/0092006 A1* | 4/2014 | Boelter | G06F 3/013 345/156 |
| 2014/0274391 A1* | 9/2014 | Stafford | G02B 27/0081 463/32 |
| 2014/0340644 A1 | 11/2014 | Haine et al. | |

OTHER PUBLICATIONS

International Search Report and Written Opinion from International Application No. PCT/US2015/064095, dated Mar. 1, 2016, 14 pp.

Second Written Opinion from International Application No. PCT/US2015/064095, dated Nov. 23, 2016, 8 pp.

* cited by examiner

VISION CORRECTION THROUGH GRAPHICS PROCESSING

BACKGROUND

Computing devices and display devices continue to become smaller and more lightweight, allowing for more powerful processing in smaller packages. Lightweight devices with powerful capabilities allow technology to become more integrated with users' everyday lives. For instance, the power and display capabilities of past desktop computers may now be found in cellular telephones, laptop computers, tablet computers, and even in wearable computing devices, such as wrist-mounted devices (e.g., smartwatches) and head-mounted devices.

Visual content displayed by such devices, such as content for graphical user interfaces and video games, may be generated by a graphics processing unit (GPU). A GPU may convert two-dimensional (2D) or three-dimensional (3D) objects into a 2D pixel representation that may be displayed. In order to generate content for display, GPUs may perform various operations or commands to process images.

SUMMARY

This disclosure presents systems, techniques methods, and apparatuses for determining parameter modifications for graphics image generation and generating corrected graphics images based on the modified parameters. More specifically, the techniques described herein may enable a computing device to provide output to and receive feedback from a user in order to determine modification values that can be used to generate graphics images that account for users' eyesight imperfections, thereby producing graphics images that appear sharper and more in-focus to users who do not have perfect eyesight.

In one example of the disclosure, a method of graphics processing includes outputting for display, by a computing device, a plurality of test graphics images, receiving, by the computing device, input indicative of a perception of a user of the computing device of at least one test graphics image from the plurality of test graphics images, determining, by the computing device and based at least in part on the received input, at least one parameter modification value, and generating, by the computing device, a corrected graphics image based at least in part on the at least one parameter modification value.

In another example of the disclosure, an apparatus configured for graphics processing includes a memory configured to store graphics data and one or more processors in communication with the memory, the one or more processors configured to output, for display, a plurality of test graphics images, receive input indicative of a perception of a user of the computing device of at least one test graphics image from the plurality of test graphics images, determine, based at least in part on the received input, at least one parameter modification value, and generate a corrected graphics image based at least in part on the at least one parameter modification value.

In another example, this disclosure describes a computer-readable storage medium storing instructions that, when executed, cause one or more processors of a device configured for graphics processing to output, for display, a plurality of test graphics images, receive input indicative of a perception of a user of the computing device of at least one test graphics image from the plurality of test graphics images, determine, based at least in part on the received input, at least one parameter modification value, and generate a corrected graphics image based at least in part on the at least one parameter modification value.

In another example, this disclosure describes an apparatus configured to process graphics, the apparatus including means for outputting, for display, a plurality of test graphics images, means for receiving input indicative of a perception of a user of the computing device of at least one test graphics image from the plurality of test graphics images, means for determining, based at least in part on the received input, at least one parameter modification value, and means for generating a corrected graphics image based at least in part on the at least one parameter modification value.

The details of one or more examples are set forth in the accompanying drawings and the description below. Other features, objects, and advantages will be apparent from the description and drawings, and from the claims.

DETAILED DESCRIPTION

For users without perfect eyesight, such as those who use contact lenses, glasses, or other vision correction implements, viewing content displayed to some display devices may be an unpleasant experience. For instance, wearing glasses may render the use of certain wearable devices (e.g., a head-mounted display device) almost impossible for some users. Without wearing corrective lenses, content displayed to the head-mounted display device may not appear as crisply to the users as it should. An inability to see the displayed content clearly may degrade the user experience.

Techniques of the present disclosure may enable display of content that appears sharper and clearer to users who have less-than-perfect eyesight by processing the content to account for vision imperfections of a user. That is, the techniques described herein may reduce the need for external vision correction by enabling more accurate display of content that compensates for a user's vision problems. By reducing the need for glasses, contacts, or other vision correction implements, the techniques of the present disclosure may allow users with less-than-perfect eyesight to more easily and comfortably interact with various types of computing devices and display devices, thereby improving the user experience.

Figure 1:
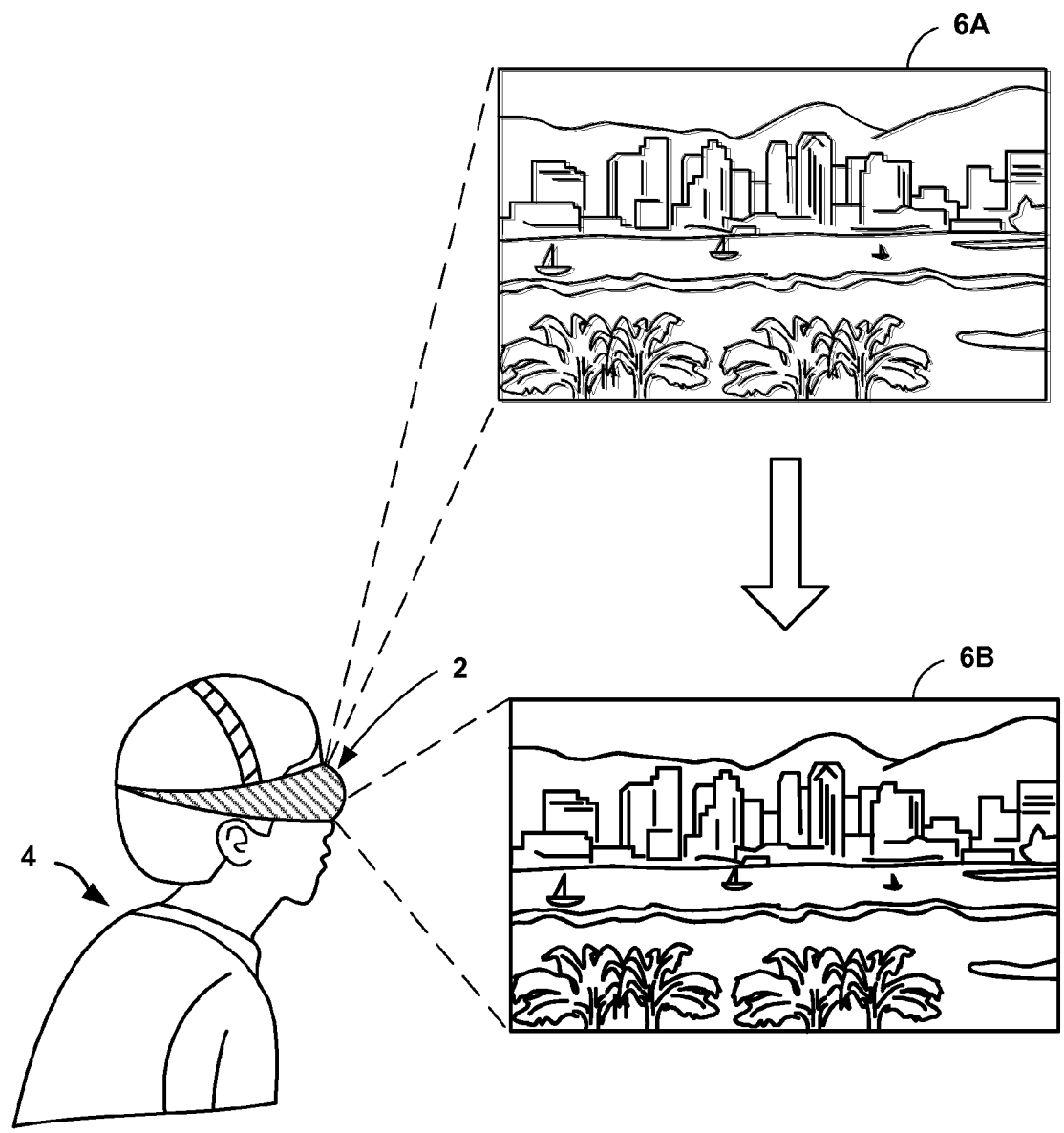
FIG. 1 is a conceptual diagram illustrating an example computing environment including a computing device that is configured to implement the techniques of the present disclosure.

FIG. 1 is a conceptual diagram illustrating an example computing environment that includes a computing device 2 configured to implement the techniques of this disclosure. In the example of FIG. 1, computing device 2 is a wearable computing device that a user (e.g., user 4) may mount on the user's head for use. In other examples, computing device 2 may be external to the wearable display. Computing device 2 may have a goggles form factor, a visor form factor, a glasses form factor, or otherwise be usable to view content displayed to one or more displays of computing device 2. In other examples, computing device 2 may be another type of wearable device (e.g., a wrist-mounted computing device, etc.), a personal computer, a desktop computer, a laptop computer, a tablet computer, a computer workstation, a video game platform or console, a mobile telephone (e.g., a cellular or satellite telephone), a landline telephone, an Internet telephone, a handheld device such as a portable video game device or a personal digital assistant (PDA), a personal music player, a video player, a display device, a television, a television set-top box, a server, an intermediate network device, a mainframe computer, any mobile device, or any other type of device that processes and/or displays graphical data.

In the example of FIG. 1, computing device 2 may include one or more displays to which graphical content (e.g., one or more graphics images) may be displayed. Examples of a display or display device may include a monitor, a television, a projection device, a liquid crystal display (LCD), a plasma display panel, a light emitting diode (LED) array, such as an organic LED (OLED) display, a cathode ray tube (CRT) display, electronic paper, a surface-conduction electron-emitted display (SED), a laser television display, a nanocrystal display or another type of display unit. Each display of computing device 2 may viewable by an eye of user 4. That is, computing device 2 may include two displays configured such that, when worn and used properly, a left display of computing device 2 is visible to the left eye of user 4, and a right display of computing device 2 is visible to the right eye of user 4. In other examples, computing device 2 may include a single display, three displays, or more. In some examples, computing device 2 may not include a display. That is, in some examples, computing device 2 may be operable to generate content to be displayed to one or more display devices external to computing device 2. In some such examples, computing device 2 may be operable to store generated content and/or send generated content to one or more display devices operatively coupled to computing device 2 (e.g., via one or more wired and/or wireless connections).

User 4, in the example of FIG. 1, may have less-than-perfect vision. For instance, user 4 may suffer from myopia (i.e., nearsightedness). In order to account for the user's eyesight, user 4 may, in the example of FIG. 1, regularly wear glasses. Many forms of imperfect eyesight (e.g., myopia or nearsightedness, hyperopia or farsightedness, astigmatism, and/or other vision imperfections) may result in vision being blurry, out-of-focus, and/or out of proportion due to the focal point of light entering the user's eye occurring at a spot other than the user's retina. That is, light that enters the eye is focused (e.g., by elements of the user's eye) at the wrong place. Myopia, for instance, is the result of light being focused before the retina. Vision correction implements such as glasses, contact lens, and monocles may compensate for various vision imperfections by modifying the direction of light entering the eye, such that the modified light is focused at the retina. Thus, using glasses may generally enable user 4 to see more clearly than without the user's glasses.

Wearing glasses, however, may make wearable computing devices or display devices, such as computing device 2, difficult or uncomfortable to use. In the example of FIG. 1, for instance, user 4 may be unable to wear computing device 2 over the user's glasses. Thus, in order to use computing device 2, user 4 may remove the glasses. In some examples, users may be unable or unwilling to wear contact lenses or other vision correction implements. For instance, some users' vision may be affected in a minor way and the users may opt to live without vision correction. Regardless of the reason, users with imperfect vision may desire to use a computing device or display device without using vision correction implements. However, without vision correction implements, content displayed to the user may appear blurry or out of focus.

Graphics image 6A illustrates one example of how a displayed graphics image may appear to a user with less-than-perfect eyesight when the user is not wearing any vision correction implements. For instance, graphics image 6A may be displayed by computing device 2 to the left display, visible to the left eye of user 4. When user 4 views graphics image 6A at the left display, the user's left eye may be unable to properly focus the light received from the left display. Thus, graphics image 6A may appear blurry and out-of-focus. That is, while the graphics image may be crystal clear at the left display, user 4's left eye may be unable to focus the light, received from the display, on to the retina of the user's left eye, and thus the crystal clear image may appear blurry to user 4.

In accordance with the techniques described herein, computing device 2 may be configured to determine one or more ways in which to modify content to be displayed in order to compensate for the particular vision imperfections of user 4. That is, computing device 2 may determine how to process content to account for imperfections in the vision of user 4 (e.g., myopia, hyperopia, astigmatism, and/or other conditions) and thereby provide user 4 with images that appear crisper and clearer to user 4.

In order to properly account for a user's vision imperfections, computing device 2 may allow a user to provide feedback or input indicative of the user's vision problems. In the example of FIG. 1, for instance, computing device 2 may provide a graphical user interface (GUI) or physical control with which user 4 may interact in order to provide information indicative of the vision imperfections of user 4. In various examples, computing device 2 may allow users to input different information for each eye, different information for two or more axes (e.g., a first value for a first axis and a second value for a second axis) of one or both eyes, different information for different portions (e.g., regions) of a display, or otherwise provide precise information indicative of the user's particular vision conditions.

In some examples, computing device 2 may be configured to explicitly receive user eyesight correction values (e.g., a corrective lens prescription). For instance, computing device 2 may be configured to receive magnification values (e.g., for correcting myopia and hyperopia) in diopters, focal lengths, or other units. Computing device 2 may additionally or alternatively be configured to receive an angle value (e.g., for correcting astigmatism) associated with one or more magnification values. The angle value may be specified in degrees, radians, meridians, or other units. In some examples, computing device 2 may use one or more approximation tables to determine parameter modification values based on received user eyesight correction values. For instance, computing device 2 may use an approximation table that specifies—for a particular level of myopia—a corresponding increase (or decrease) in any level of blurring that is to be applied to graphics images.

In some examples, computing device 2 may provide a user interface, such as a graphical user interface (GUI), to assist users in providing information about their vision imperfections. Users may be able to interact with computing device 2 via the user interface and provide input (e.g., feedback). For instance, computing device 2 may output one or more simple graphics images for display to user 4. Computing device 2 may receive information (e.g., input by user 4) indicating how the displayed graphics images are perceived by user 4. Received information may, in various examples, be a simple indication of whether or not the image is acceptable (e.g., "yes" or "no"), an indication of whether a currently displayed graphics image is better or worse than a previously displayed graphics image, an indication of a location or region of a displayed graphics image that is perceived as incorrect, or other information about user 4's perception of the graphics image.

Computing device 2 may use information derived from the received feedback when generating graphics images for display. For instance, computing device 2 may modify values used by vertex and/or pixel/fragment shaders when generating graphics images and/or to perform post processing on generated graphics images, thereby distorting the images such that, when displayed to a display, the content appears more in-focus to the user. That is, graphics images generated using parameters that are modified based on received user input may appear distorted to those having perfect vision but, by distorting the graphics images in a fashion and to an extent that is in accordance with the vision imperfections of a particular user, the graphics images may appear more in-focus and/or clearer to the particular user.

In some examples, the image processing techniques described herein may take advantage of ray tracing principles to provide for a vision-corrected image. For instance, each graphics image to be displayed to a display device can be represented as rays of light passing through a focal point or focal plane (e.g., the display surface). These rays of light can be quantized down to a ray per pixel of the display. By re-negotiating the paths for the rays of light, the content to be displayed can be distorted in order to determine a new end-location of a given pixel based on a user's provided input. In other words, instead of a fixed focal plane at the viewport (e.g., the screen of a display), applying the techniques described herein may move the plane based on the received prescription information, thereby bringing graphics images more "into focus" for users with imperfect vision.

Graphics image 6B illustrates one example of how a graphics image, modified using the techniques described herein and displayed by computing device 2, may appear to user 4 when user 4 is not wearing any vision correction implements. For instance, graphics image 6B may be displayed by computing device 2 to the left display, visible to the left eye of user 4. When user 4 views graphics image 6B at the left display, the user's left eye may be continue to improperly focus the light received from the left display. However, because the graphics image was modified based on user 4's input (e.g., indicating the degree to which user 4's left eye is affected by myopia), the light received from the display showing graphics image 6B may better focus at the retina of user 4's left eye. Thus, graphics image 6B may appear less blurry and more in-focus to user 4. That is user 4's left eye may still be unable to focus the received light on to the retina of the user's left eye, but because the graphics image was processed to account for such inability, graphics image 6B may appear clearer and sharper to user 4.

In other words, techniques of the present disclosure may assist a user in "tuning" the application of the techniques described herein to determine the correct parameter values to use during image processing. For instance, computing device 2 may provide an "optometrist mode" in which a user may be prompted to answer a series of questions (e.g., "Which is better: option 1 or option 2?") in order to determine the parameter values. Thus, computing device 2 may enable users to accurately specify how to better process images that account for the users' eyesight imperfections, even when the users do not know their eyeglass prescription or specific eyesight problems.

Thus, in some examples, computing device 2 may be configured to process graphics images to account for a user's eyesight without the user having to enter any prescription values. In other words, computing device 2 may, in various examples, provide the optometrist mode to determine the proper parameter values to correct for a user's eyesight (e.g., without previously having received any indication of prescription values for the user), or to perfect the parameter values (e.g., to verify and/or improve specified prescription values).

The techniques of the present disclosure may, in various examples, be used to adapt content displayed to a single display device and to multiple display devices. For instance, while described in the example of FIG. 1 as being applied to content displayed to the left display of computing device 2, the techniques described herein may additionally or alternatively applied to content displayed to the right display of computing device 2. Furthermore, the techniques described herein may, in some examples, be applied to stereo content. Stereo content may be content displayed in a stereo fashion (e.g., to simulate a three dimensional environment). Stereo content may be displayed as two sets of content to single display device (e.g., "3DTV") or as a first set of content to a first display (e.g., visible to a left eye of the user) and a second set of content to a second display (e.g., visible to a right eye of the user). In some examples, the processing techniques described herein may be independently applied to each set of content to compensate for different vision maladies in each of a user's eyes. In the example of FIG. 1, for instance, user 4 may be more myopic in the user's left eye than in the user's right eye. Thus, computing device 2 may apply stronger processing to the content displayed to the left display of computing device 2 and apply weaker processing to the content displayed to the right display of computing device 2.

Figure 2:
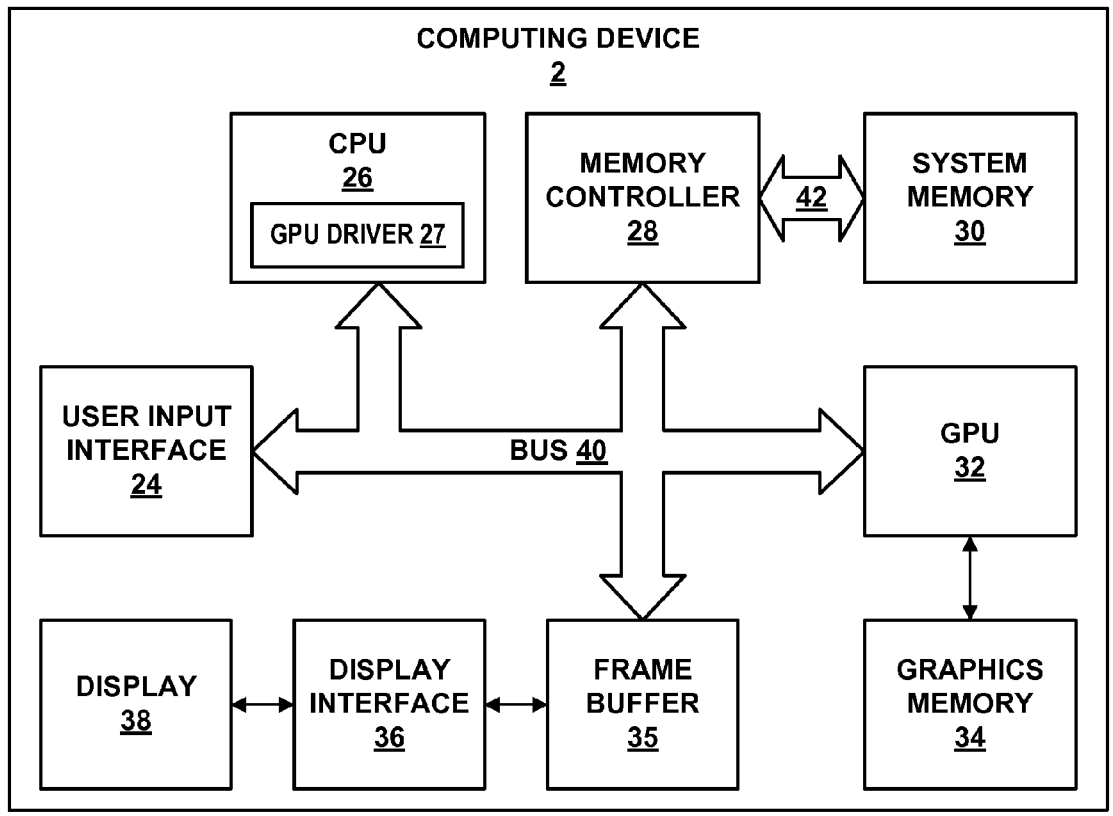
FIG. 2 is a block diagram illustrating further details of the example computing device shown in FIG. 1.

FIG. 2 is a block diagram illustrating further details of computing device 2 as shown in FIG. 1. That is, in the example of FIG. 2, computing device 2 may be configured to obtain information indicative of user eyesight imperfections, determine parameter modification values based on the obtained information, and process graphics images to be displayed such that displayed content appears in-focus to users who do not have perfect eyesight. As illustrated in the example of FIG. 2, computing device 2 includes user input interface 24, central processing unit (CPU) 26, memory controller 28, system memory 30, graphics processing unit (GPU) 32, graphics memory 34, display interface 36, display 38 and buses 40 and 42. While GPU 32 and graphics memory 34 are shown in the example of FIG. 2 as separate components, graphics memory 34 may, in some examples, be "on-chip" with GPU 32. In some examples, all hardware elements show in FIG. 2 may be on-chip (e.g., in a system on a chip (SoC) design).

User input interface 24, CPU 26, memory controller 28, GPU 32 and display interface 36 may communicate with each other using bus 40. Memory controller 28 and system memory 30 may also communicate with each other using bus 42. Buses 40, 42 may be any of a variety of bus structures or other communication links, such as a third generation bus (e.g., a HyperTransport bus or an InfiniBand bus), a second generation bus (e.g., an Advanced Graphics Port bus, a Peripheral Component Interconnect (PCI) Express bus, an Advanced eXentisible Interface (AXI) bus), or any other type of bus or interconnection capable of communicating information. It should be noted that the specific configuration of components, buses, and communication interfaces shown in the example of FIG. 2 is merely exemplary, and other configurations of computing devices and/or other graphics processing systems with the same or different components may be used to implement the techniques of this disclosure.

In the example of FIG. 2, CPU 26 may comprise a general-purpose or a special-purpose processor that controls operation of computing device 2. A user may provide input to computing device 2 to cause CPU 26 to execute one or more software applications. The software applications that execute on CPU 26 may include, for example, an operating system, a word processor application, an email application, a spread sheet application, a media player application, a video game application, a graphical user interface application or any other program. Additionally, CPU 26 may execute a GPU driver 27 for controlling the operation of GPU 32. In some examples, the user may provide input to computing device 2 via one or more input devices (not shown) such as a keyboard, a mouse, a microphone, a touch pad or another input device that is coupled to computing device 2 via user input interface 24.

The software applications that execute on CPU 26 may include one or more graphics rendering instructions that instruct CPU 26 to cause the rendering of a graphics image for display to display 38. In some examples, the instructions may conform to a graphics application programming interface (API), such as, e.g., an Open Graphics Library (OpenGL®) API, an Open Graphics Library Embedded Systems (OpenGL ES) API, a Direct3D API, an X3D API, a RenderMan API, a WebGL API, or any other public or proprietary standard graphics API. In order to process the graphics rendering instructions, CPU 26 may issue one or more graphics rendering commands to GPU 32 (e.g., through GPU driver 27) to cause GPU 32 to perform some or all of the rendering of the graphics data. In some examples, the graphics data to be rendered may include a list of graphics primitives, e.g., points, lines, triangles, quadrilaterals, triangle strips, etc.

Memory controller 28, in the example of FIG. 2, may facilitate the transfer of data going into and out of system memory 30. For example, memory controller 28 may receive memory read and write commands, and service such commands with respect to system memory 30 in order to provide memory services for the components in computing device 2. Memory controller 28 is communicatively coupled to system memory 30 via memory bus 42. Although illustrated in FIG. 2 as being a processing module that is separate from both CPU 26 and system memory 30, some or all of the functionality of memory controller 28 may, in some examples, be implemented on one or both of CPU 26 and system memory 30.

In the example of FIG. 2, system memory 30 may store program modules and/or instructions that are accessible for execution by CPU 26 and/or data for use by the programs executing on CPU 26. For instance, system memory 30 may store a window manager application that is used by CPU 26 to present a graphical user interface (GUI) on display 38. In addition, system memory 30 may store user applications and application surface data associated with the applications. System memory 30 may additionally store information for use by and/or generated by other components of computing device 2. For instance, system memory 30 may act as a device memory for GPU 32 and may store data to be operated on by GPU 32 as well as data resulting from operations performed by GPU 32. In various examples, system memory 30 may store any combination of texture buffers, depth buffers, stencil buffers, vertex buffers, frame buffers, or the like. System memory 30 may include one or more volatile or non-volatile memories or storage devices, such as, for example, random access memory (RAM), static RAM (SRAM), dynamic RAM (DRAM), read-only memory (ROM), erasable programmable ROM (EPROM), electrically erasable programmable ROM (EEPROM), Flash memory, a magnetic data media or an optical storage media.

GPU 32, in the example of FIG. 2, may be configured to perform graphics operations to render one or more graphics primitives to display 38. Thus, when one of the software applications executing on CPU 26 requires graphics processing, CPU 26 may provide graphics commands and graphics data to GPU 32 for rendering to display 38. The graphics data may include drawing commands, state information, primitive information, texture information, or other data. GPU 32 may, in some examples, be built with a highly-parallel structure that provides more efficient processing of complex graphic related operations than CPU 26. For instance, GPU 32 may include a plurality of processing elements that are configured to operate on multiple vertices or pixels in a parallel manner. A highly-parallel structure may allow GPU 32 to draw graphics images (e.g., GUIs and two dimensional (2D) and/or three dimensional (3D) graphics scenes) to display 38 more quickly than drawing the images directly to display 38 using CPU 26.

GPU 32 may, in some examples, be integrated into a motherboard of computing device 2. In other examples, GPU 32 may be present on a graphics card that is installed in a port in the motherboard of computing device 2 or may be otherwise incorporated within a peripheral device configured to interoperate with computing device 2. GPU 32 may include one or more processors, such as one or more microprocessors, application specific integrated circuits (ASICs), field programmable gate arrays (FPGAs), digital signal processors (DSPs), or other equivalent integrated or discrete logic circuitry.

As shown in the example of FIG. 2, GPU 32 may be directly coupled to graphics memory 34. Thus, GPU 32 may read data from and write data to graphics memory 34 without using bus 40. In other words, GPU 32 may process data locally using a local storage, instead of off-chip memory. This may allow GPU 32 to operate in a more efficient manner by eliminating the need of GPU 32 to read and write data via bus 40, which may experience heavy bus traffic. In some examples, however, GPU 32 may not include a separate memory, but instead utilize system memory 30 via bus 40. Graphics memory 34 may include one or more volatile or non-volatile memories or storage devices, such as, e.g., random access memory (RAM), static RAM (SRAM), dynamic RAM (DRAM), erasable programmable ROM (EPROM), electrically erasable programmable ROM (EEPROM), Flash memory, a magnetic data media or an optical storage media.

CPU 26 and/or GPU 32 may store rendered graphics images as image data in a frame buffer 35. Frame buffer 35 may be an independent memory or may be allocated within system memory 30. Display interface 36 may retrieve the image data from frame buffer 35 and configure display 38 to display the graphics image represented by the rendered image data. In some examples, display interface 36 may include a digital-to-analog converter (DAC) that is configured to convert the digital values retrieved from frame buffer 35 into an analog signal consumable by display 38. In other examples, display interface 36 may pass the digital values directly to display 38 for processing. Display 38 may include a monitor, a television, a projection device, a liquid crystal display (LCD), a plasma display panel, a light emitting diode (LED) array, such as an organic LED (OLED) display, a cathode ray tube (CRT) display, electronic paper, a surface-conduction electron-emitted display (SED), a laser television display, a nanocrystal display or another type of display unit. As shown in the example of FIG. 2, display 38 may, in some examples, be integrated within computing device 2. For instance, display 38 may be a screen of a mobile telephone or a head-mounted computing device. Alternatively, display 38 may, in some examples, be a standalone device coupled to computing device 2 via a wired or wireless communications link. For instance, display 38 may be a computer monitor or flat panel display connected to a personal computer or other computing device via a cable or wireless link.

According to one example of the disclosure, CPU 26 and/or GPU driver 27 may be configured to generate rendering commands for rendering a graphics image. GPU 32 may be configured to execute the rendering commands and render a corrected graphics image based at least in part on input indicative of user eyesight imperfections. In some examples, GPU 32 may be configured to render the corrected graphics image as part of executing the rendering commands. That is, at least a portion of the rendering commands may cause GPU 32 to render the graphics image using parameters that are modified based on the received input. In some examples, GPU 32 may be configured to render the corrected graphics image by post processing a graphics image. That is, the rendering commands may cause GPU 32 to apply post processing using modified parameters to generate the corrected graphics image. In other words, GPU 32 may, in various examples, render a corrected graphics images as part of the rendering process and/or during post processing of the graphics image.

Figure 3:
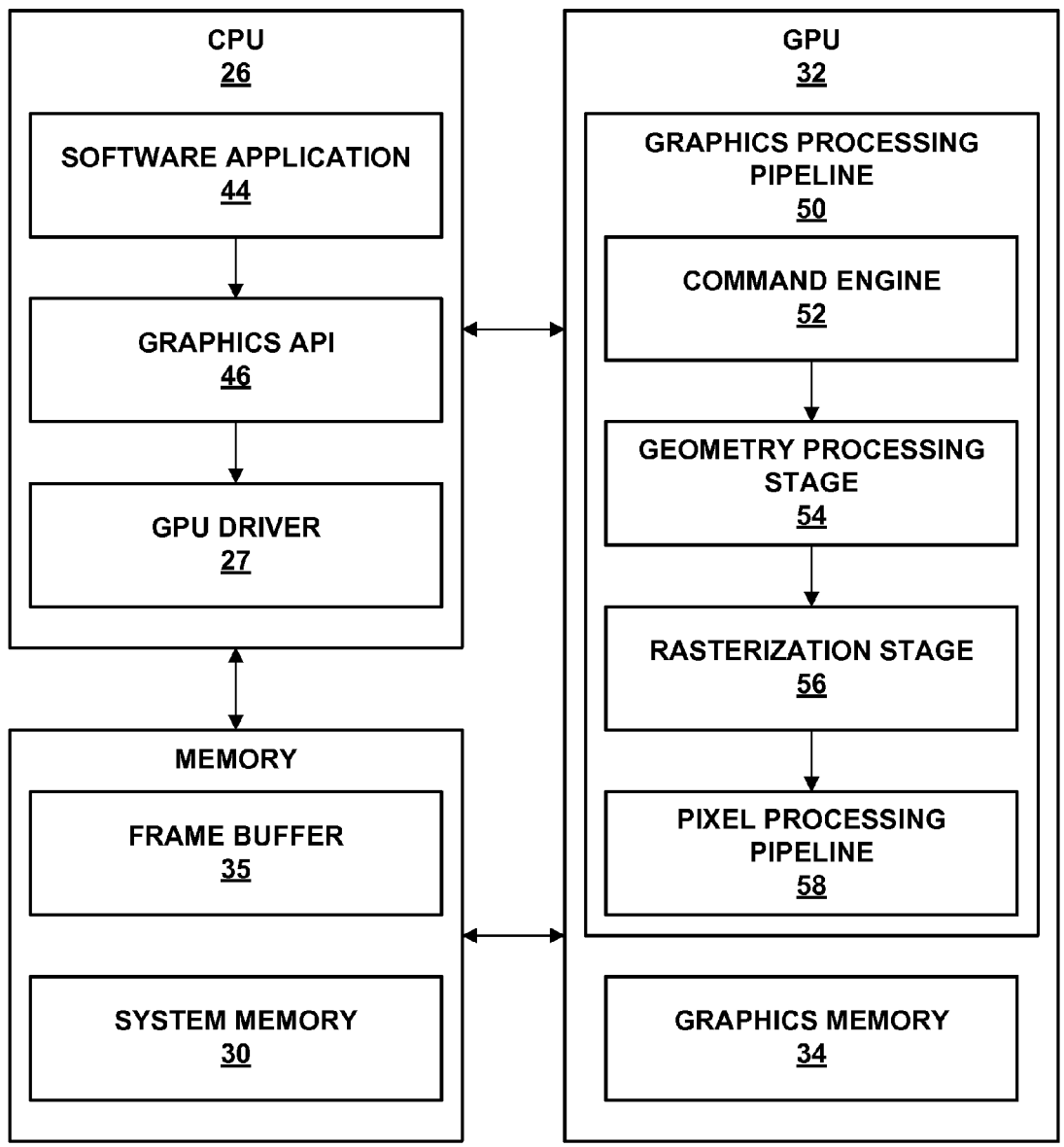
FIG. 3 is a block diagram illustrating example processing units configured to implement the techniques of the present disclosure.

FIG. 3 is a block diagram illustrating one example of processing units (e.g., CPU 26, GPU 32, and system memory 30 of FIG. 2) configured to implement the techniques of this disclosure. In the example of FIG. 3, CPU 26 may include at least one software application 44, a graphics API 46, and a GPU driver 27, each of which may be one or more software applications or services that execute on CPU 26. GPU 32 may include a graphics processing pipeline 50 that includes a plurality of graphics processing stages that operate together to execute graphics processing commands. GPU 32 may be configured to execute graphics processing pipeline 50 to render corrected graphics images based at least in part on input indicative of user eyesight imperfections. For instance, GPU 32 may account for the eyesight imperfections of the user during the rendering process and/or during a post-processing step. As shown in the example of FIG. 3, graphics processing pipeline 50 may include a command engine 52, a geometry processing stage 54, a rasterization stage 56, and a pixel processing pipeline 58. Each of the components in graphics processing pipeline 50 may be implemented as fixed-function components, programmable components (e.g., as part of a shader program executing on a programmable shader unit), or as a combination of fixed-function and programmable components. Memory available to CPU 26 and GPU 32 may include system memory 30 and frame buffer 35. Frame buffer 35 may be a part of system memory 30 or may be separate from system memory 30. Frame buffer 35 may store rendered image data.

Software application 44 may be any application that utilizes the functionality of GPU 32. For example, software application 44 may be a GUI application, an operating system, a portable mapping application, a computer-aided design program for engineering or artistic applications, a video game application, or another type of software application that uses 2D or 3D graphics.

Software application 44 may include one or more drawing instructions that instruct GPU 32 to render a graphical user interface (GUI) and/or a graphics scene. For example, the drawing instructions may include instructions that define a set of one or more graphics primitives to be rendered by GPU 32. In some examples, the drawing instructions may, collectively, define all or part of a plurality of windowing surfaces used in a GUI. In additional examples, the drawing instructions may, collectively, define all or part of a graphics scene that includes one or more graphics objects within a model space or world space defined by the application.

Software application 44 may invoke GPU driver 27, via graphics API 46, to issue one or more commands to GPU 32 for rendering one or more graphics primitives into a displayable graphics image. For example, software application 44 may invoke GPU driver 27, via graphics API 46, to provide primitive definitions to GPU 32. In some instances, the primitive definitions may be provided to GPU 32 in the form of a list of drawing primitives, e.g., triangles, rectangles, triangle fans, triangle strips, etc. The primitive definitions may include vertex specifications that specify one or more vertices associated with the primitives to be rendered. The vertex specifications may include positional coordinates for each vertex and, in some instances, other attributes associated with the vertex, such as, e.g., color coordinates, normal vectors, and texture coordinates. The primitive definitions may also include primitive type information (e.g., triangle, rectangle, triangle fan, triangle strip, etc.), scaling information, rotation information, and the like.

Based on the instructions issued by software application 44 to GPU driver 27, GPU driver 27 may formulate one or more commands that specify one or more operations for GPU 32 to perform in order to render the primitive. When GPU 32 receives a command from CPU 26, graphics processing pipeline 50 decodes the command and configures one or more processing elements within graphics processing pipeline 50 to perform the operation specified in the command. After performing the specified operations, graphics processing pipeline 50 outputs the rendered data to frame buffer 35 associated with a display device (e.g., display 38).

GPU driver 27 may be further configured to compile one or more shader programs, and to download the compiled shader programs onto one or more programmable shader units contained within GPU 32. The shader programs may be written in any shading language. The compiled shader programs may include one or more instructions that control the operation of a programmable shader unit within GPU 32. For example, the shader programs may include vertex shader programs and/or pixel shader programs. A vertex shader program may control the execution of a programmable vertex shader unit or a unified shader unit, and include instructions that specify one or more per-vertex operations. A pixel shader program may include pixel shader programs that control the execution of a programmable pixel shader unit or a unified shader unit, and include instructions that specify one or more per-pixel operations. In accordance with some example embodiments of this disclosure, a pixel shader program may also include instructions that selectively cause texture values to be retrieved for source pixels based on corresponding destination alpha values for the source pixels.

Graphics processing pipeline 50 may be configured to receive one or more graphics processing commands from CPU 26, via GPU driver 27, and to execute the graphics processing commands to generate a displayable graphics image. As discussed above, graphics processing pipeline 50 includes a plurality of stages that operate together to execute graphics processing commands. It should be noted, however, that such stages need not necessarily be implemented in separate hardware blocks. For example, portions of geometry processing stage 54 and pixel processing pipeline 58 may be implemented as part of a unified shader unit.

Command engine 52 may receive graphics processing commands and configure the remaining processing stages within graphics processing pipeline 50 to perform various operations for carrying out the graphics processing commands. The graphics processing commands may include, for example, drawing commands and graphics state commands. The drawing commands may include vertex specification commands that specify positional coordinates for one or more vertices (e.g., of an object or primitive in 3D space) and, in some instances, other attribute values associated with each of the vertices, such as, e.g., color coordinates, normal vectors, texture coordinates and fog coordinates. The graphics state commands may include primitive type commands, transformation commands, lighting commands, etc. The primitive type commands may specify the type of primitive to be rendered and/or how the vertices are combined to form a primitive. The transformation commands may specify the types of transformations to perform on the vertices. The lighting commands may specify the type, direction and/or placement of different lights within a graphics scene. Command engine 52 may cause geometry processing stage 54 to perform geometry processing with respect to vertices and/or primitives associated with one or more received commands.

Geometry processing stage 54 may perform per-vertex operations and/or primitive setup operations on one or more vertices in order to generate primitive data for rasterization stage 56. Each vertex may be associated with a set of attributes, such as, e.g., positional coordinates, color values, a normal vector, and texture coordinates. Geometry processing stage 54 modifies one or more of these attributes according to various per-vertex operations. For example, geometry processing stage 54 may perform one or more transformations on vertex positional coordinates to produce modified vertex positional coordinates. Geometry processing stage 54 may, for example, apply one or more of a modeling transformation, a viewing transformation, a projection transformation, a ModelView transformation, a ModelViewProjection transformation, a viewport transformation and a depth range scaling transformation to the vertex positional coordinates to generate the modified vertex positional coordinates. In some instances, the vertex positional coordinates may be model space coordinates, and the modified vertex positional coordinates may be screen space coordinates. The screen space coordinates may be obtained after the application of the modeling, viewing, projection and viewport transformations. In some instances, geometry processing stage 54 may also perform per-vertex lighting operations on the vertices to generate modified color coordinates for the vertices. Geometry processing stage 54 may also perform other operations including, e.g., normal transformations, normal normalization operations, view volume clipping, homogenous division and/or backface culling operations.

In some examples, all or part of geometry processing stage 54 may be implemented by one or more shader programs executing on one or more shader units. For example, geometry processing stage 54 may be implemented, in such examples, by a vertex shader, a geometry shader or any combination thereof. In other examples, geometry processing stage 54 may be implemented as a fixed-function hardware processing pipeline or as a combination of fixed-function hardware and one or more shader programs executing on one or more shader units.

In some examples, in order to generate a graphics image that corrects for user eyesight imperfections, geometry processing stage 54 may use a modified transformation matrix to transform vertices' 3D positions in virtual space to 2D coordinates at which the vertices should appear in a rendered image. That is, geometry processing stage 54 may process data that defines one or more 3D objects using a transformation matrix composed of one or more modified parameters to generate the graphics image. The modified parameters may be determined based on the received information indicative of user eyesight imperfections. For instance, geometry processing stage 54 may multiply one or more parameters of the transformation matrix by a determined parameter modification value and/or add a determined parameter modification value to one or more parameters in order to create the modified transformation matrix. By using a modified transformation matrix, the resulting output of geometry processing stage 54 may be different than it would be had the transformation matrix parameters not been modified based on the user eyesight imperfections.

Geometry processing stage 54 may produce primitive data that includes a set of one or more modified vertices that define a primitive to be rasterized as well as data that specifies how the vertices combine to form a primitive. Each of the modified vertices may include, for example, modified vertex positional coordinates and processed vertex attribute values associated with the vertex. The primitive data may collectively correspond to a primitive to be rasterized by further stages of graphics processing pipeline 50. Conceptually, each vertex may correspond to a corner of a primitive where two edges of the primitive meet. Geometry processing stage 54 may provide the primitive data to rasterization stage 56 for further processing.

Rasterization stage 56 is configured to receive, from geometry processing stage 54, primitive data that represents a primitive to be rasterized, and to rasterize the primitive to generate a plurality of source pixels that correspond to the rasterized primitive. In some examples, rasterization stage 56 may determine which screen pixel locations are covered by the primitive to be rasterized, and generate a source pixel for each screen pixel location determined to be covered by the primitive. Rasterization stage 56 may determine which screen pixel locations are covered by a primitive by using techniques known to those of skill in the art, such as, e.g., an edge-walking technique, evaluating edge equations, etc. Rasterization stage 56 may provide the resulting source pixels to pixel processing pipeline 58 for further processing.

The source pixels generated by rasterization stage 56 may correspond to a screen pixel location, e.g., a destination pixel, and be associated with one or more color attributes. All of the source pixels generated for a specific rasterized primitive may be said to be associated with the rasterized primitive. The pixels that are determined by rasterization stage 56 to be covered by a primitive may conceptually include pixels that represent the vertices of the primitive, pixels that represent the edges of the primitive and pixels that represent the interior of the primitive.

Pixel processing pipeline 58 is configured to receive a source pixel associated with a rasterized primitive or fragment, and to perform one or more per-pixel operations on the source pixel. Per-pixel operations that may be performed by pixel processing pipeline 58 include, e.g., alpha test, texture mapping, color computation, pixel shading, per-pixel lighting, fog processing, blending, a pixel ownership text, a source alpha test, a stencil test, a depth test, a scissors test and/or stippling operations. In addition, pixel processing pipeline 58 may execute one or more pixel shader programs or fragment shader programs to perform one or more per-pixel or per-fragment operations. The resulting data produced by pixel processing pipeline 58 may be referred to herein as destination pixel data and stored in frame buffer 35. The destination pixel data may be associated with a destination pixel in frame buffer 35 that has the same display location as the source pixel that was processed. The destination pixel data may include data such as, e.g., color values, destination alpha values, depth values, etc.

Frame buffer 35 stores destination pixels for GPU 32. Each destination pixel may be associated with a unique screen pixel location. In some examples, frame buffer 35 may store color components and a destination alpha value for each destination pixel. For example, frame buffer 35 may store Red, Green, Blue, Alpha (RGBA) components for each pixel where the "RGB" components correspond to color values and the "A" component corresponds to a destination alpha value. Although frame buffer 35 and system memory 30 are illustrated as being separate memory units, in other examples, frame buffer 35 may be part of system memory 30.

In some examples, one or more components of graphics processing pipeline 50 may be configured to receive post-processing commands from CPU 26, via GPU driver 27, and to execute the post-processing commands to modify a graphics image based on input indicative of user eyesight imperfections. For instance, command engine 52 may receive commands specifying a graphics image (e.g., a collection of destination pixels stored at frame buffer 35) and configure one or more of the remaining components of graphics processing pipeline 50 (e.g., pixel processing pipeline 58) to execute the commands. The pixel shaders and/or fragment shaders of pixel processing pipeline 58 may, in some examples, apply a deconvolution filter, a blurring filter, or other image effects to the graphics image to account for user eyesight. Parameters for such filters or effects may be determined based on input indicative of eyesight imperfections. Thus, the output of the pixel shaders and/or fragment shaders of pixel processing pipeline 58 may appear more clear to a user than if the post processing was not performed. That is, by performing various filtering operations and/or other post processing on the graphics image, shaders of pixel processing pipeline 58 may provide a graphics image that is actually more corrupted (e.g., blurred), but that may be perceived, by a user that has imperfect eyesight, as more correct.

In this way, GPU 32 may be configured to render a corrected graphics image based on input indicative of user eyesight imperfections. In some examples, GPU 32 may utilize parameters modified based on the input as part of executing rendering commands. In some examples, GPU 32 may utilize parameters modified based on the input as part of post-processing the graphics image. Further examples and details regarding use of such parameters are provided below in FIGS. 4-6.

Figure 4:
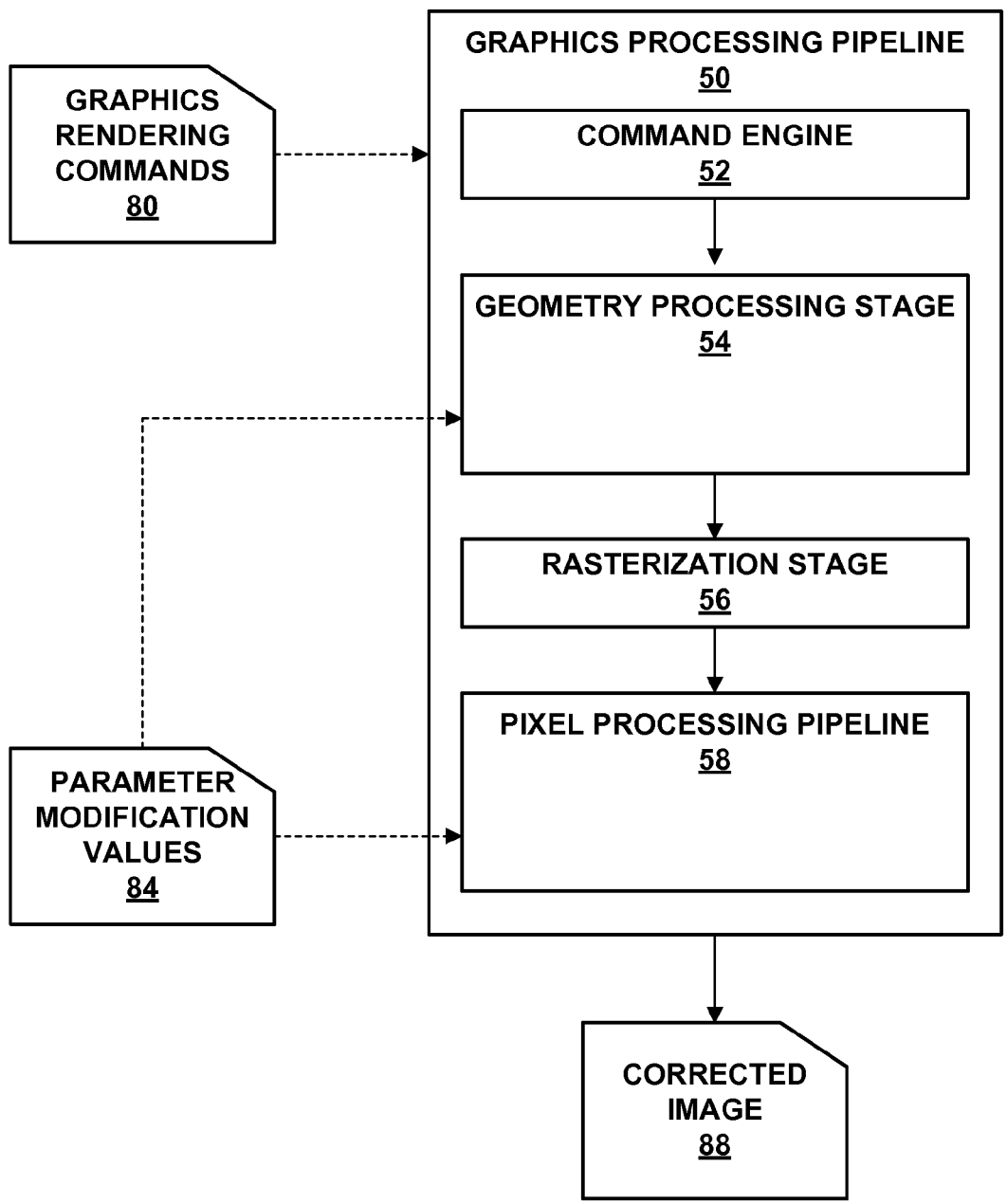
FIG. 4 is a block diagram illustrating an example process implementing one or more techniques of the present disclosure.

FIG. 4 is a block diagram illustrating an example process implementing one or more techniques of the present disclosure. For purposes of illustration only, the example process of FIG. 4 is described below within the context of FIGS. 1-3. In the example of FIG. 4, computing device 2 may be configured to generate a graphics image using parameters that are modified based on input indicative of a user's eyesight imperfections. That is, computing device 2 may receive input indicative of the user's eyesight imperfections, determine appropriate parameter modification values, and, during rendering of a graphics image, use parameters modified in accordance with the parameter modification values.

Graphics processing pipeline 50, in the example of FIG. 4, may execute graphics rendering commands 80. Graphics rendering commands 80 may correspond to a request (e.g., by an application executing at computing device 2) for a rendered graphics image. Graphics rendering commands 80 may, in some examples, include drawing commands and graphics state commands. In the example of FIG. 4, graphics rendering commands 80 may include one or more graphics state commands to cause the requested rendering to take into account a user's eyesight imperfections. For instance, graphics rendering commands 80 may include calls to an API of one or more components of graphics processing pipeline 50 (e.g., geometry processing stage 54 and/or pixel processing stage 58) thereby indicating that the requested graphics image is rendered in a fashion that compensates for the user's eyesight.

As one example, graphics rendering commands 80 may include a shader instruction that would be inserted into an appropriate geometry processing shader. Such a shader instruction may be used by GPU driver 27 to insert commands to render the corresponding graphics image using parameters that are modified based on information indicative of the user's eyesight imperfections. As another example, graphics rendering commands 80 may include a function call to post-process the position output from a shader. Such a function call may be useful in the case where an application has simple shaders, and does not want to modify the shader content.

In the example of FIG. 4, command engine 52 may receive graphics rendering commands 80 and configure one or more other components of graphics processing pipeline 50 to execute graphics rendering commands 80. For instance, command engine 52 may configure geometry processing stage 54 to perform transformations using modified parameters and/or may configure pixel processing pipeline 58 to perform filtering using modified parameters. In the example of FIG. 4, command engine 52 may cause both geometry processing stage 54 and pixel processing pipeline 58 to utilize modified parameters. In some examples, command engine 52 may cause one of geometry processing stage 54 or pixel processing pipeline 58 to perform operations using modified parameters. That is, in various examples, generation of a corrected graphics image may include the use of modified parameters during a geometry processing stage (e.g., to perform operations on vertices or other geometric objects) and/or during a pixel processing stage (e.g., to perform operations on pixels, etc.).

As part of processing graphics rendering commands 80, geometry processing stage 54 and/or pixel processing pipeline 58 may receive or otherwise obtain parameter modification values 84. For instance, GPU 32 may receive parameter modification values 84 from CPU 26, or may obtain parameter modification values 84 from system memory 30. Parameter modification values 84 may specify a value or values that geometry processing stage 54 and/or pixel processing pipeline 58 may use to modify parameters involved in rendering a graphics image. In some examples, parameter modification values 84 may be values, coefficients, or other modifiers of a transformation matrix, values, coefficients, or other modifiers of a filter, or other indications of how to modify parameters to account for a user's vision imperfections.

In the example of FIG. 4, for instance, geometry processing stage 54 may be configured to perform one or more transformations using parameters that are modified based on parameter modification values 84. Such transformations may include transforming Model Space into World Space, transforming World Space into Camera Space, and/or transforming Camera Space into Homogeneous Space (or Projection Space). Each transformation may utilize a set of parameters (e.g., a transformation matrix) to transform image data (e.g., vertices of a model) from one space to another. For instance, transforming Model Space into World Space may be accomplished by applying a Model matrix to each vertex of a model.

A Model matrix may, in some examples, be a matrix usable to modify the values of a vertex of an object in order to move the object in a space. The Model matrix may be composed of a number of underlying matrices, such as a translation matrix, T, one or more rotation matrices R, and a scaling matrix, S, as shown below.

$$T = \begin{bmatrix} 1 & 0 & 0 & T_x \\ 0 & 1 & 0 & T_y \\ 0 & 0 & 1 & T_z \\ 0 & 0 & 0 & 1 \end{bmatrix}$$

$$R_x = \begin{bmatrix} 1 & 0 & 0 & 0 \\ 0 & \cos(\alpha) & -\sin(\alpha) & 0 \\ 0 & \sin(\alpha) & \cos(\alpha) & 0 \\ 0 & 0 & 0 & 1 \end{bmatrix} \quad R_y = \begin{bmatrix} \cos(\alpha) & 0 & \sin(\alpha) & 0 \\ 0 & 1 & 0 & 0 \\ -\sin(\alpha) & 0 & \cos(\alpha) & 0 \\ 0 & 0 & 0 & 1 \end{bmatrix}$$

$$R_z = \begin{bmatrix} \cos(\alpha) & -\sin(\alpha) & 0 & 0 \\ \sin(\alpha) & \cos(\alpha) & 0 & 0 \\ 0 & 0 & 1 & 0 \\ 0 & 0 & 0 & 1 \end{bmatrix}$$

$$S = \begin{bmatrix} S_x & 0 & 0 & 0 \\ 0 & S_y & 0 & 0 \\ 0 & 0 & S_z & 0 \\ 0 & 0 & 0 & 1 \end{bmatrix}$$

As can be seen in the examples above, the underlying matrices of the Model matrix include parameter values defining how vertices of the object are to be modified in order to increase or decrease the size of the object (e.g., the $S_x$, $S_y$, and $S_z$ parameters), rotate the object (e.g., the $\alpha$ parameter), and/or move the object (e.g., $T_x$, $T_y$, and $T_z$ parameters). Thus, the resulting Model matrix may be used to scale, rotate, and translate vertices of an object in one transformation. By changing the parameter values of the underlying matrices, the resulting Model matrix may be modified, and the object will be transformed differently than if the parameter values were unchanged. In other words, parameter modification values 84 may indicate that one or more of $S_x$, $S_y$, $S_z$, $\alpha$, $T_x$, $T_y$, or $T_z$ should be changed before transforming vertices as part of rendering a graphics image.

In a similar fashion, transforming World Space into Camera Space may be accomplished by applying a View matrix to vertices in the World Space. Modifying parameter values of the View matrix (or matrices that make up the View matrix) will modify the way that the World Space is transformed.

Transforming Camera Space into Homogenous Space (or Projection Space) may be accomplished using a Projection matrix. An example projection matrix, P, is shown below.

$$P = \begin{bmatrix} \dfrac{2 \times \text{near}}{\text{right} - \text{left}} & 0 & \dfrac{\text{right} + \text{left}}{\text{right} - \text{left}} & 0 \\ 0 & \dfrac{2 \times \text{near}}{\text{top} - \text{bottom}} & \dfrac{\text{top} + \text{bottom}}{\text{top} - \text{bottom}} & 0 \\ 0 & 0 & -\dfrac{\text{far} + \text{near}}{\text{far} - \text{near}} & -\dfrac{2 \times (\text{far} - \text{near})}{\text{far} - \text{near}} \\ 0 & 0 & 0 & 1 \end{bmatrix}$$

Modifying parameters of the Projection matrix will also change the way in which the Camera Space is transformed. For instance, if parameter modification values 84 specify a modifier for the "near" value shown in the Projection matrix above, this will modify the way in which the projection is displayed on a display by modifying the location of the near plane for transforming content to the Homogeneous Space. Modifying the "near" value shown in the Projection matrix above may correspond to modifying a focal point for objects displayed in the resulting graphics image. That is, the near parameter may define the focal plane of the image.

In the example of FIG. 4, geometry processing stage 54 may account for various user eyesight imperfections by rendering graphics images using parameters modified based on parameter modification values 84. For instance, a user may be using a head-mounted computing device having two displays—one for each eye. The user may have trouble focusing correctly on the same location of a stereo graphics image with both eyes. In such example, computing device 2 may employ the techniques described herein to determine parameter modification values 84 that include a parameter modification value for a horizontal translation parameter and/or a vertical translation parameter. Geometry processing stage 54 may apply parameter modification values 84 to base values of the horizontal and/or vertical translation parameters to create a modified transformation matrix and thereby render graphics images that account for the poor focus experienced by the user. That is, one or both displays may display graphics images that are modified to be "centered" for the respective eye of the user. Various other parameter modification values may be used by geometry processing stage 54, including horizontal, vertical, or depth scaling parameter modification values, horizontal, vertical, or depth translation parameter modification values, rotation parameter modification values, near plane location parameter modification values, or other parameter modification values.

Pixel processing pipeline 58 may, in the example of FIG. 4, be configured to perform one or more operations using parameters that are modified based on parameter modification values 84. Such operations may include the application of various blurring filters, de-blurring filters (e.g., deconvolution filters), or other filters. Operations may also include application of transformations, such as operations to transform pixels based on radial distortion, based on lens projections (e.g., transformations that correct for characteristics of optical lenses), and other transformations. Such operations may depend on various parameters, such as parameters indicating the level of blur or deconvolution to be applied, the size of the lens to use for a lens projection or lens compensation projection, and any other value that can be modified to modify the resulting pixels.

As a result of performing the transformations and filters using modified parameter values, graphics processing pipeline 50 may render a corrected graphics image, such as corrected image 88. In accordance with the techniques of the present disclosure, corrected image 88 may account for a level of user eyesight correction, thereby providing the user with a graphics image that appears more correct to the user, even when the user does not have perfect vision and is not wearing vision correction implements such as glasses or contacts. By exposing a vision correction API to applications executing at computing device 2 and rendering graphics images using parameter values that are modified based on input indicative of a user's eyesight imperfections, the techniques described herein may allow computing device 2 to more accurately account for the user's eyesight.

Figure 5:
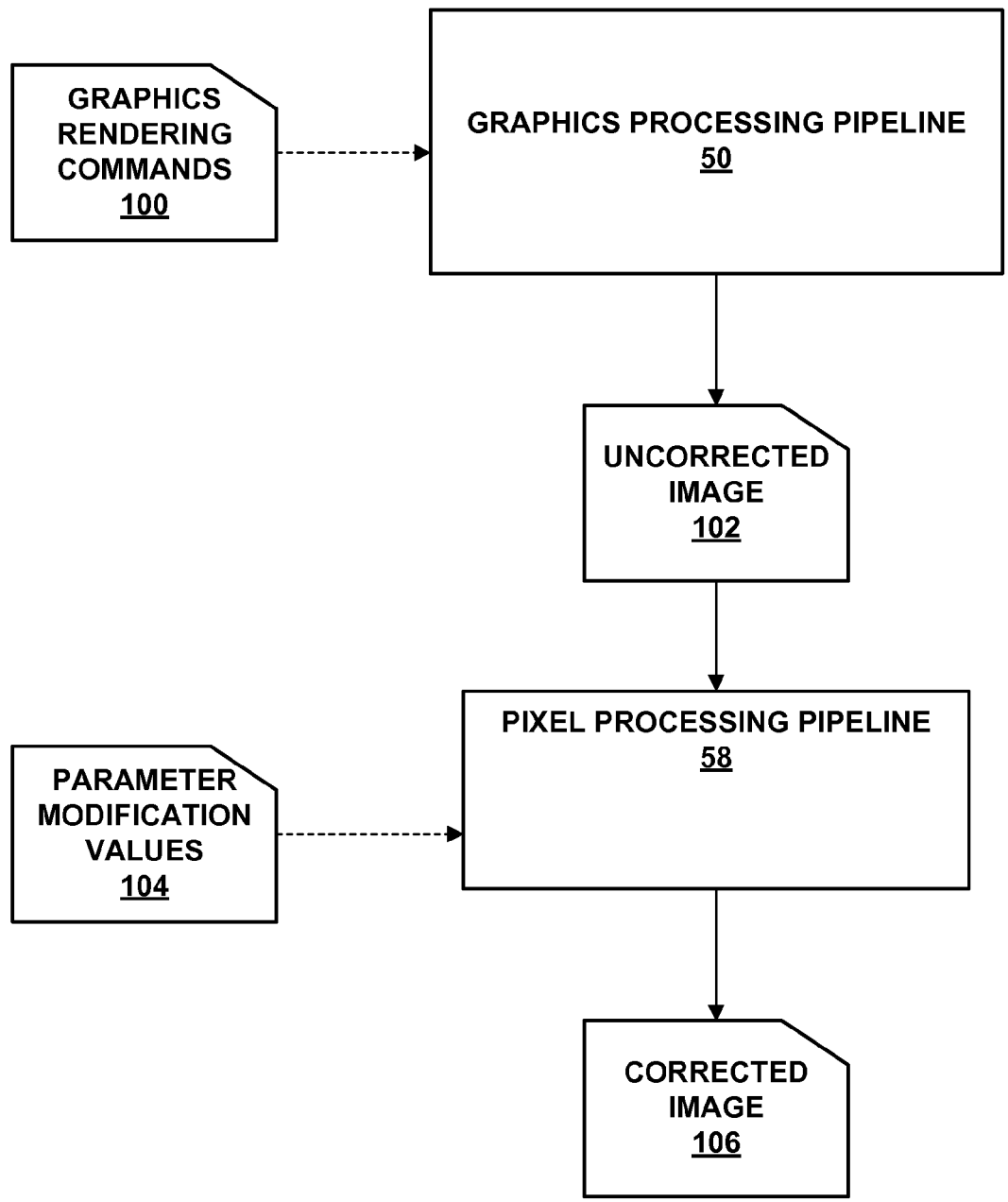
FIG. 5 is a block diagram illustrating the example process implementing one or more techniques of the present disclosure.

FIG. 5 is a block diagram illustrating an example process implementing one or more techniques of the present disclosure. For purposes of illustration only, the example process of FIG. 4 is described below within the context of FIGS. 1-3. In the example of FIG. 5, computing device 2 may be configured to generate a corrected graphics image by applying post processing to a graphics image using parameters that are modified based on input indicative of a user's eyesight imperfections. That is, computing device 2 may receive input indicative of the user's eyesight imperfections, determine appropriate parameter modification values, and use parameters that are modified based on the values to post process a graphics image to produce a corrected graphics image.

Graphics processing pipeline 50, in the example of FIG. 5, may execute graphics rendering commands 100. Graphics rendering commands 100 may correspond to a request (e.g., by an application executing at computing device 2) for a rendered graphics image. By executing graphics rendering commands 100, graphics processing pipeline 50 may render uncorrected image 102.

In the example of FIG. 5, uncorrected image 102 may represent a graphics image that does not compensate for users' eyesight imperfections. That is, uncorrected image 102 may, if displayed to a display device, appear in-focus to users having perfect vision but appear out-of-focus or otherwise incorrect to those users that do not have perfect vision. In some examples, after rendering uncorrected image 102, GPU 32 may store uncorrected image 102 (e.g., within graphics memory 34).

GPU 32 may, in the example of FIG. 5, utilize pixel processing pipeline 58 of graphics processing pipeline 50 to modify uncorrected image 102 to account for a user's eyesight maladies. For instance, GPU 32 may cause pixel processing pipeline 58 to perform post processing based on parameters determined using parameter modification values 104. Post processing may include the various operations performable by pixel processing pipeline 58 as described above with respect to FIG. 4. That is, in the example of FIG. 5, pixel processing pipeline 58 may be operable to apply various filters to the pixel data, perform various transformations on the pixel data (e.g., to compensate for or apply lens projections), and other operations.

Post processing using parameters determined based on parameter modification values 104 may produce corrected image 106. In accordance with the techniques of the present disclosure, corrected image 106 may account for a level of user eyesight imperfection, thereby providing the user with a graphics image that appears more correct to the user, even when the user does not have perfect vision and is not wearing vision correction implements such as glasses or contacts. By utilizing a post-processing step to modify a rendered uncorrected image and generate a corrected image, the techniques described herein may enable a computing device to correct for a user's eyesight impairment without participation by applications. That is, by generating corrected graphics images through post processing, the user eyesight correction process may be application-agnostic.

Figure 6:
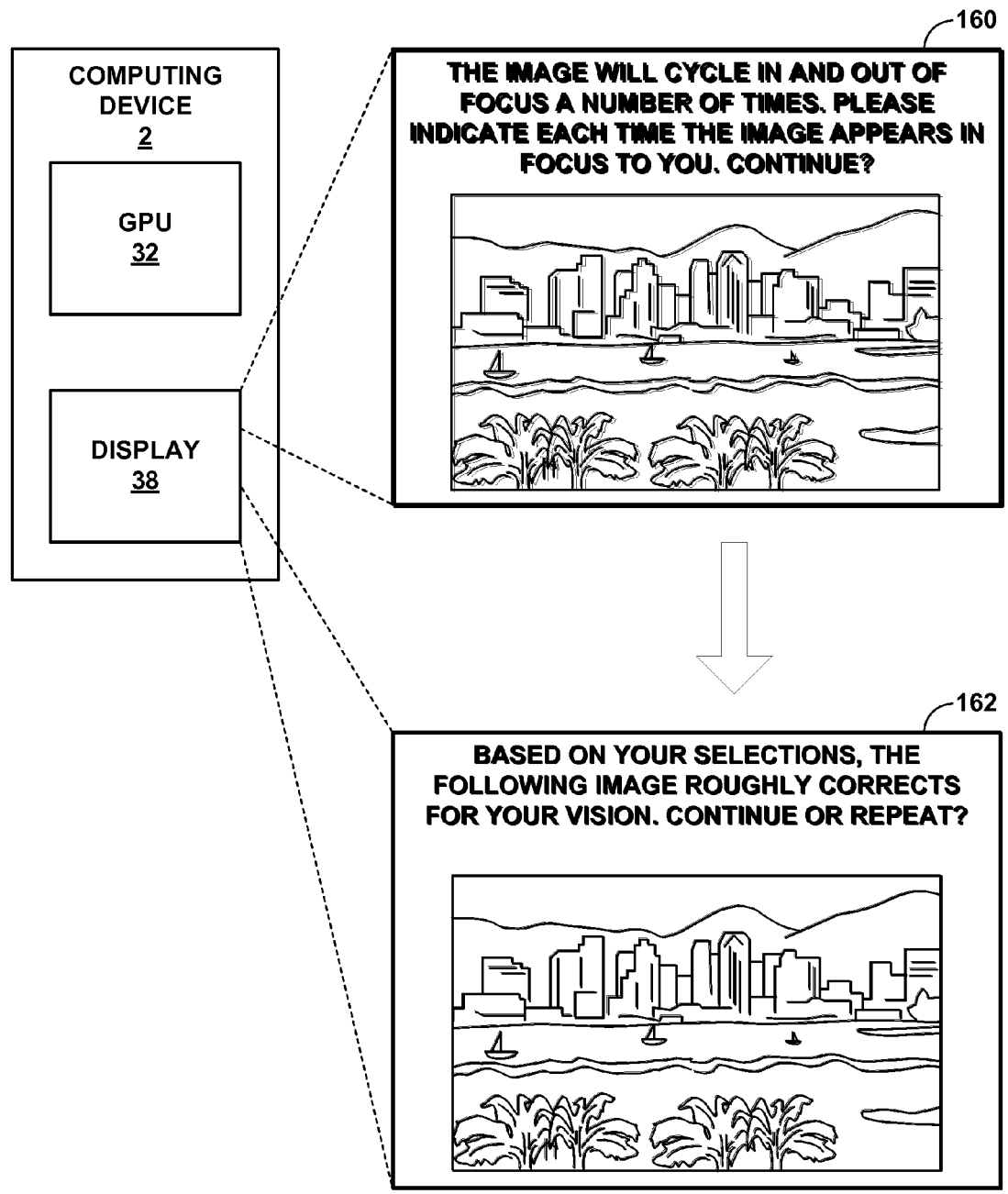
FIG. 6 is a block diagram illustrating an example computing device and graphics images for obtaining information indicative of user eyesight imperfections in accordance with the techniques of the present disclosure.

FIG. 6 is a block diagram illustrating an example computing device 2 and graphics images 160 and 162 for obtaining information indicative of user eyesight imperfections in accordance with the techniques of the present disclosure. For purposes of illustration only, the example of FIG. 6 is described below within the context of FIGS. 1-3.

Computing device 2, as shown in the example of FIG. 6, may be configured to output graphics images 160 and 162 as part of a GUI for obtaining feedback indicative of user eyesight imperfections. The feedback received may be used to determine parameter modification values that are usable to determine parameters used in rendering graphics images that appear more correct to a user. That is, the process described in the example of FIG. 6 may enable a user of computing device 2 to provide input that computing device 2 can use to determine modified parameters for rendering graphics images. In some examples, such as when computing device 2 includes two or more displays (e.g., stereo displays of a headset), the process described in the example of FIG. 6 may be performed for each display. That is, computing device 2 may determine one or more parameter modification values for each display (e.g., corresponding to respective eyes of the user). In some examples, the process described in the example of FIG. 6 may be performed on one or more portions of a display (e.g., not on the display as a whole, but instead on particular regions or portions).

In the example of FIG. 6, GPU 32 may render graphics image 160 for display to display 38. For instance, display 38 may output graphics image 160 during a user's initial setup and configuration of computing device 2 or in response to computing device 2 receiving user input instructing computing device 2 to determine the user's eyesight imperfections (e.g., by accessing a settings configuration application executed by computing device 2). GPU 32 may not correct for user eyesight imperfections when rendering graphics image 160. That is, graphics image 160 may be rendered without taking any imperfections in the user's vision into account. Thus graphics image 160 may appear blurry or out-of-focus to a user having imperfect vision.

Responsive to displaying graphics image 160 to display 38, computing device 2 may, in the example of FIG. 6, receive user input instructing computing device 2 to continue with the eyesight correction determination. For instance, the user may press a button (e.g., a physical button, a user interface element displayed to a touch-sensitive or presence-sensitive display, etc.) of computing device 2, press a button of a device communicatively coupled to computing device 2, speak a voice command (e.g., "Continue," "Okay," etc.) or otherwise indicate to computing device 2 that the user wishes to continue.

In the example of FIG. 6, responsive to receiving input from the user instructing computing device 2 to continue, computing device 2 may cause the displayed graphics image to incrementally change in some fashion. For instance, GPU 32 may render progressive versions of graphics image 160 for output to display 38, while using incrementally different parameter values for a blurring filter (e.g., applied by pixel processing pipeline 58). For instance, GPU 32 may render a first version of graphics image 160 using extremely small parameter values and display 38 may display the first version. Each version of graphics image 160 may be displayed for a short time (e.g., 0.5 seconds, 1 second, 2 seconds, or other duration).

GPU 32 may render a second version of graphics image 160 using parameter values that are slightly increased from that used in rendering the first version and display 38 may display the second version. For instance, if GPU 32 renders the first version using a value of 0.1 for a parameter indicating a level of blur to be applied (e.g., on a scale of 0-10), GPU 32 may render the second version using a parameter value of 0.2. This incremental increase may continue until GPU 32 renders a version of graphics image 160 using a defined maximum parameter value (e.g., 10.0). Once a defined maximum parameter value is reached, GPU 32 may begin rendering versions of graphics image 160 using incrementally smaller parameter values. In this way, computing device 2 may display a graphics image that cycles through various degrees of image modification. In some examples, computing device 2 may cycle through each parameter once (e.g., from a minimum value to a maximum value). In some examples, computing device 2 may cycle through each parameter multiple times (e.g., from a minimum value to a maximum value and then back to a minimum).

In some examples, computing device 2 may cycle through more than one parameter for each version of graphics image 160. For instance, GPU 32 may render versions of graphics image 160 while cycling through a first parameter corresponding to scaling of a horizontal axis of graphics image 160 and then while cycling through a second parameter corresponding to scaling of a vertical axis of graphics image 160. As another example, GPU 32 may render versions of graphics image 160 while cycling through a first parameter that is involved in a blurring filter, as well as a second parameter that is involved in a deconvolution filter. In this way, computing device 2 may display a graphics image that also cycles through compensation for various degrees and/or types of vision afflictions.

As computing device 2 displays versions of graphics images 160 rendered using progressively increasing or decreasing parameter values, computing device 2 may, in the example of FIG. 6, receive input from a user when the user believes that the displayed graphics image appears better (e.g., more in-focus, more properly proportioned, or otherwise improved). For instance, the user may push a button, provide voice input, or otherwise provide an indication to computing device 2 when a currently displayed version of graphics image 160 appears better than the other displayed versions. In some examples, computing device 2 may receive a single indication. In other examples, such as when computing device 2 cycles through values multiple times, computing device 2 may receive multiple indications, providing a small range of possible parameter values.

In the example of FIG. 6, computing device 2 may determine approximate parameter modification values based on the received indications. For instance, when computing device 2 receives a single indication that the displayed graphics image appears in-focus, computing device 2 may determine the approximate parameter modification value or values as the parameter value or values used to render the graphics image displayed when the indication was received. As another example, when computing device 2 receives two or more indications that the displayed graphics image appears in-focus, computing device 2 may determine the approximate parameter modification value or values as the average of each value that was used to render the respective graphics image displayed when each indication was received. In yet other examples, computing device 2 may determine the approximate parameter modification values as the values having the most corresponding indications, or in some other fashion. In other words, computing device 2 may determine one or more approximate parameter modification values based on the received indications.

GPU 32 may render graphics image 162 using parameter values determined based on the approximate parameter modification value or values and display 38 may output the approximately corrected graphics image for display. Thereafter, computing device 2 may receive input instructing computing device 2 to repeat the process or input instructing computing device 2 to continue with the determined approximate parameter modification value or values. For instance, computing device 2 may receive input (e.g., a press of a button, voice input, etc.) instructing computing device 2 to proceed to determining more exact parameter modification values, based on the determined approximate value or values.

In this way, computing device 2 may enable the user to provide information indicative of eyesight imperfections and may determine parameter modification values for use in rendering graphics images without the user having to manually enter values. This may be useful when, for instance, the user does not know the user's eyeglass prescription or have knowledge of various graphics processing techniques. Additionally, while the distance between display 38 and the user's eye may be factored in when determining parameter modification values, a fixed approximation may be used in the example process of FIG. 6.

Figure 7:
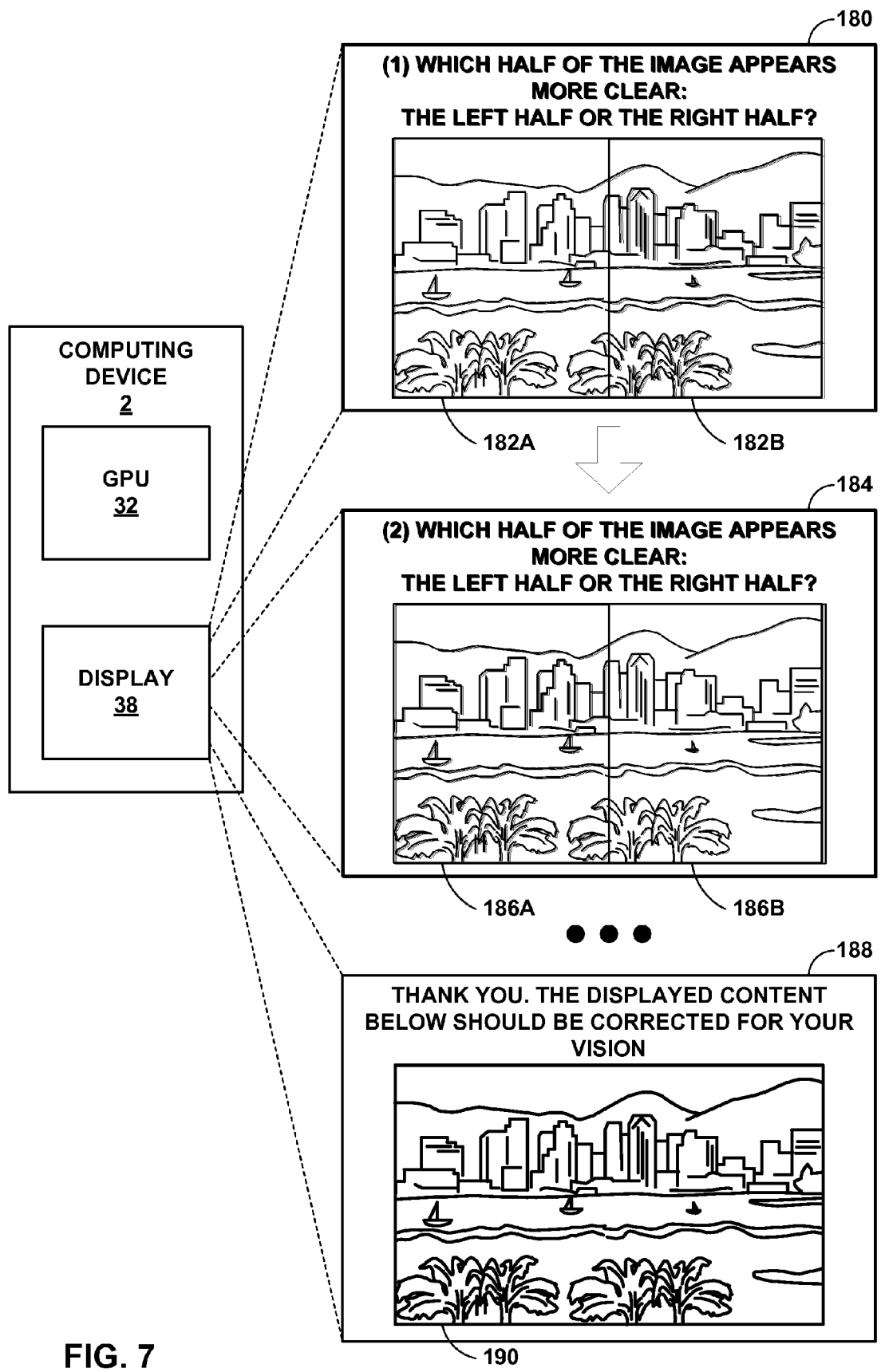
FIG. 7 is a block diagram illustrating an example computing device and graphics images for obtaining information indicative of user eyesight imperfections in accordance with the techniques of the present disclosure.

FIG. 7 is a block diagram illustrating an example computing device 2 and graphics images 180, 184, and 186 for obtaining information indicative of user eyesight imperfections in accordance with the techniques of the present disclosure. For purposes of illustration only, the example of FIG. 7 is described below within the context of FIGS. 1-3.

Computing device 2, as shown in the example of FIG. 7, may be configured to output graphics images 180, 184, and 186 as part of a GUI for obtaining feedback indicative of user eyesight imperfections by guiding a user through a series of selections to choose the parts of images that appear more correct. The feedback received may be used to determine parameter modification values that may be taken into account when rendering subsequent graphics images in order to make the subsequent graphics images appear more correct to the user. In some examples, the process described in the example of FIG. 7 may enable a user of computing device 2 to "fine tune" parameter modification values. The process of FIG. 7 may enable computing device 2 to provide clearer, more in-focus graphics images to a user, in accordance with the techniques described herein. In some examples, such as when computing device 2 includes two or more displays (e.g., stereo displays), the process described in the example of FIG. 7 may be performed for each display. In other words, computing device 2 may determine one or more respective parameter modification values for each display.

In some examples, computing device 2 may perform the process described in the example of FIG. 7 subsequent to a user providing input that instructs computing device 2 to continue after performing the process described in the example of FIG. 6. In some examples, computing device 2 may perform the process described in the example of FIG. 7 responsive to receiving input (e.g., voice input, a selection of a displayed value, or other means of input) to select one or more approximate parameter modification values. That is, in some examples, computing device 2 may perform the process described in FIG. 7 to obtain exact parameter modification values from previously determined or received approximate parameter modification values. In some examples, computing device 2 may perform the process described in the example of FIG. 7 based on input instructing computing device 2 to determine parameter modification values. That is, in some examples, computing device 2 may determine specific parameter modification values without previously determining approximate values.

In the example of FIG. 7, computing device 2 may have stored an approximate modification value of 0.3 for a blurring filter parameter. That is, a user of computing device 2 may have provided input or otherwise indicated that he or she perceives images as more correct when the graphics image is subjected to a blurring filter with an additional 0.3 units more than normal. The input or indication may have been provided by the user inputting a value of 0.3, providing input that experientially indicates a value of 0.3 (or values that average to 0.3) or otherwise providing input usable to determine an approximate blurring parameter modification value of 0.3.

Based at least in part on the approximate value of 0.3, GPU 32 may, in the example of FIG. 7, render graphics image 180 for display to display 38. Graphics image 180 may include content rendered using different parameter values, from which the user may choose the "better" looking content. That is, GPU 32 may render at least two portions of graphics image 180 (e.g., portion 182A and 182B). Each portion may be rendered using different parameter values. For instance, portion 182A may be rendered using a parameter value of 0.25, while portion 182B may be rendered using a parameter value of 0.35. Consequently, one portion of the content may appear more correct to the user than the other portion.

In the example of FIG. 7, subsequent to displaying graphics image 180, computing device 2 may receive input (e.g., voice input, touch input, input using a physical button or key, or other input) indicating a selection of portion 182A. That is, the user may indicate that he or she believes that portion 182A appears better or more in-focus than portion 182B.

Based on a received selection of portion 182A, GPU 32 may, in the example of FIG. 7, render graphics image 184. Graphics image 184 includes portions 186A and 186B. Portion 186A may be rendered using a parameter value of 0.25, while portion 186B may be rendered using a value of 0.3. That is, because the user indicated that a portion of a first graphics image, rendered based on a parameter value of 0.25, appeared better than a portion of the first graphics image rendered using 0.35, computing device 2 may, in the example of FIG. 7, render portions of a second image (e.g., 186A and 186B) using values of 0.25 and 0.3 to determine whether the user's eyesight requires less correction, or whether the best correction is using a parameter modification value between 0.25 and 0.3.

In the example of FIG. 7, computing device 2 may receive input indicating a selection of portion 186B. That is, the user may indicate that content rendered using a value of 0.3 appears more accurate than content rendered using a value of 0.25. Based on the received input, computing device 2 may determine that it is likely that the user's eyesight would benefit from a parameter value nearer 0.3 than 0.25.

Subsequent to receiving the input selecting portion 186B, computing device 2 may render and display another graphics image (not shown) having portions rendered using 0.275 and 0.3. Computing device 2 may receive a selection of one of the portions (e.g., the portion rendered using 0.275). Based on the selection, computing device 2 may render and display another graphics image (not shown) having portions rendered using 0.275 and 0.288. Computing device 2 may continue in like fashion to narrow down the user's selections to an exact parameter value, outputting two portions of a graphics image that are rendered using different parameter values, receiving input selecting of one of the portions, and outputting a subsequent graphics image having portions rendered using new parameter values.

In some examples, this process may continue until the user indicates that neither portion of a graphics image looks more accurate than the other. In some examples, this process may continue until the user has gone back and forth between two values in three successive graphics images, or otherwise reached a point where any difference in parameter values is negligible (e.g. 0.1, 0.05, 0.001, or other value). In other words, the process of FIG. 7 may, in various examples, present the user with two images at a time, each image being rendered based on different values of a parameter. The parameter may continue to change values in successive images until the user stops uniquely identifying an image as "better." In some examples, the process described above may additionally or alternatively be performed using different values for other parameters (e.g., a parameter for positional translation, a parameter for a deconvolution filter, etc. to account for other vision issues). In some examples, the process may additionally or alternatively be performed using other methods of identifying eyesight imperfections of a user.

After the user has indicated that there appears to be no difference between two portions of a displayed graphics image, or otherwise provided input that causes computing device 2 to determine exact parameter modification values, GPU 32 may render graphics image 188 for display to display 38. Graphics image 188 may be rendered using the determined exact parameter modification values. Thus, graphics image 188 may appear more correct to the user. Thereafter, computing device 2 may use the determined exact parameter modification values when performing the techniques described herein to generate corrected graphics images.

Figure 8:
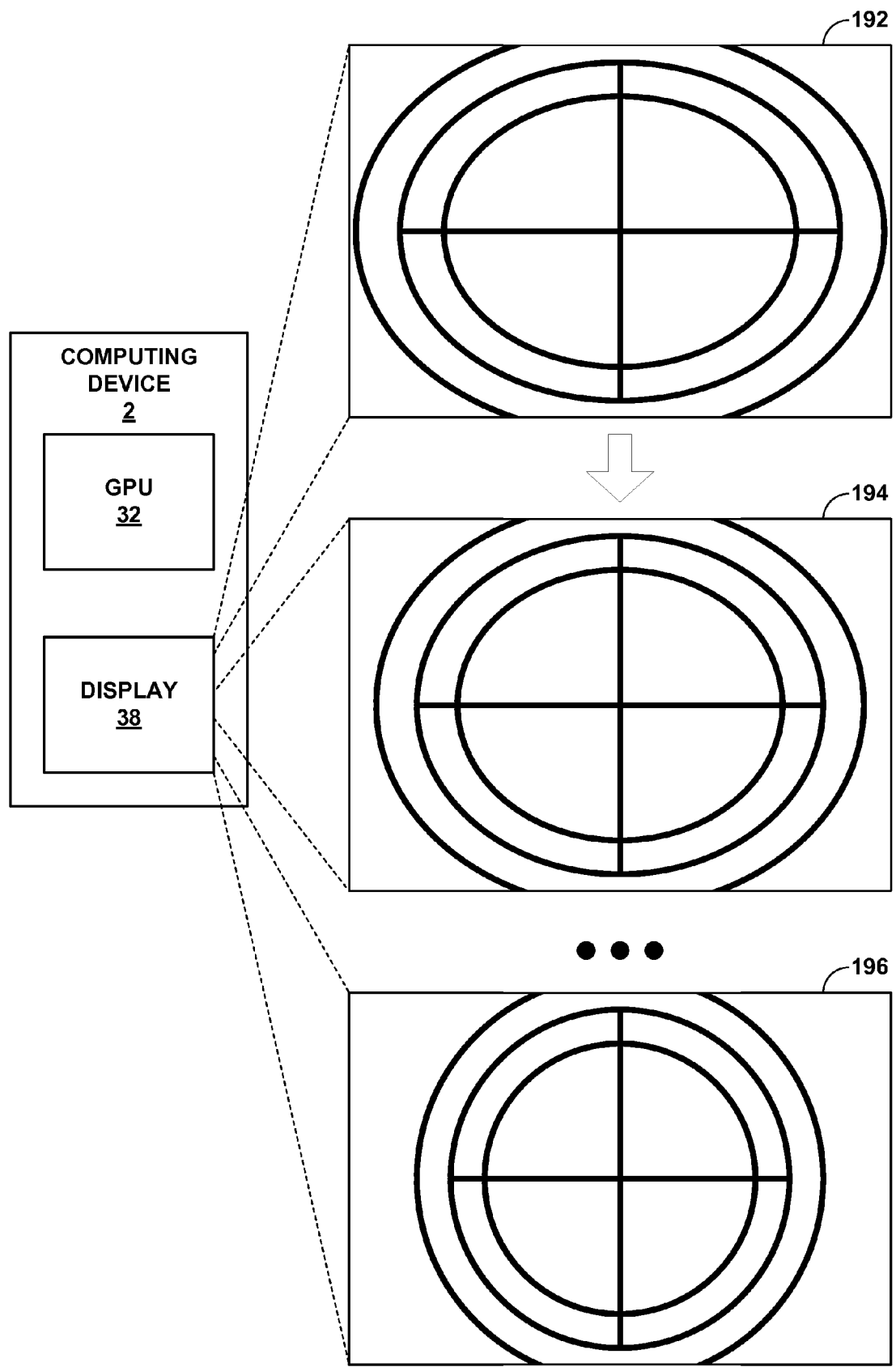
FIG. 8 is a block diagram illustrating an example computing device and graphics images for obtaining information indicative of user eyesight imperfections in accordance with the techniques of the present disclosure.

FIG. 8 is a block diagram illustrating an example computing device 2 and graphics images 190, 192, and 194 for obtaining information indicative of user eyesight imperfections in accordance with the techniques of the present disclosure. For purposes of illustration only, the example of FIG. 8 is described below within the context of FIGS. 1-3.

Computing device 2, as shown in the example of FIG. 8, may be configured to output graphics images 192, 194, and 196 as part of a GUI for obtaining feedback indicative of a user's eyesight imperfections. Computing device 2 may utilize the received feedback to determine parameter modification values. Computing device 2 and/or other computing devices may use the determined parameter modification values to determine parameter values that are usable during image rendering to generate graphics images that account for the user's eyesight imperfections.

As shown in the example of FIG. 8, graphics images 192, 194, and 196 include a number of objects. These objects may represent a set of training data that may assist the user in providing feedback indicative of the user's eyesight problems. In order to obtain useful feedback, the user may be informed beforehand of the nature of the training data. That is, computing device 2 (or a manual for computing device 2, a startup guide, or any other material) may inform the user about an object or objects that exist in the training data (e.g., shape, location, and/or other information), so that the user knows what he or she is supposed to see. In the example of FIG. 8, for instance, the user may be informed that he or she is supposed to see 3 concentric circles, two of the concentric circles being completely visible and one extending vertically off the screen, as well as two equal length, straight lines crossing the center of the circles—one horizontally and one vertically. While simple 2D objects are used in FIG. 8, training data may, in other examples, be any number of 2D and/or 3D images or video. For instance, in some examples, the training data may include 2D concentric circles drawn on a 3D sphere. In some examples, training data may be shown individually to each eye of a user. For instance, training data be shown to a left eye of a user separately from the training data shown to the right eye of the user.

In the example of FIG. 8, GPU 32 may render graphics image 192 for display to display 38. For instance, display 38 may output graphics image 192 during initial setup and configuration of computing device 2. Graphics image 192 may be rendered without taking any imperfections in the user's vision into account. Thus, graphics image 192 may appear incorrect in one or more ways to a user having imperfect vision. As seen in the example of FIG. 8, for instance, the user may have an astigmatism or other vision ailment that causes a horizontal axis to be focused differently than a vertical axis. Thus, while graphics image 192 may display three concentric circles and two equal length lines, the user may perceive three ellipses and two lines of unequal length. In other words, though data representing the three circles and two lines was rendered using unmodified transformation matrices, the resulting graphics image may appear to the user to have a larger scaling factor along the horizontal axis than along the vertical axis.

In order to determine ways in which to modify image rendering to account for the user's eyesight imperfections, computing device 2 may cause the displayed graphics image to incrementally change in various ways and obtain feedback from the user regarding the displayed images. The feedback may be indicative of the user's perception of the displayed images. For instance, GPU 32 may render progressive versions of graphics image 192 for output to display 38, while using incrementally different parameter values for various parameters of one or more transformation matrices. Computing device 2 may receive input indicating whether or not the image as perceived by the user corresponds to the description of the training data.

The example of FIG. 8 may represent one way in which computing device 2 may incrementally change graphics image 192. In the example of FIG. 8, GPU 32 may use progressively different values for a horizontal scaling parameter of a transformation matrix. If graphics image 192 is rendered using a horizontal scaling parameter value of 0, for instance, GPU 32 may render a subsequent image (e.g., graphics image 194) with a horizontal scaling parameter value of −0.2 and output the image for display. Thereafter, GPU 32 may render more graphics images (not shown) with horizontal scaling parameter values of −0.4, −0.6, −0.8, and so on.

Upon viewing one or more of the displayed images, the user may provide input indicating whether or not the displayed image aligns with what the user expects to see, given the prior description of the training data. For instance, the user may provide input indicating whether a displayed graphics image is "better" or "worse" than a previously displayed graphics image, whether the parameter that is currently being modified should be larger, smaller, or is correct as-is, or other input indicative of the user's perception of the image or images. User input may be provided in any of a number of ways, such as verbal input, a press of a button or GUI element, or other input.

In the example of FIG. 8, this process may continue, with computing device 2 outputting successive images and the user providing feedback input. In some examples, the user's perception of a displayed graphics image may eventually match the user's expectation. For instance, GPU 32 may render graphics image 196 for display. Graphics image 196 may be rendered using a horizontal scaling parameter value of −0.4.

As seen in FIG. 8, the objects in graphics image 196—in the perception of the user—may match the user's expectation, based on the description of the training data. Computing device 2 may receive user input indicating the user's satisfaction with the horizontal scaling parameter value used to render graphics image 196. Based on this input, computing device 2 may determine a modification value for the parameter. That is, based on user input indicating that a horizontal scaling parameter value resulted in the user perceiving the correct image, computing device 2 may determine a modification value for subsequent horizontal scaling parameter values. In the example of FIG. 8, for instance, computing device 2 may determine a parameter modification value of −0.6.

Thereafter, GPU 32 may modify initial parameter values based on the parameter modification values in order to determine parameter values for rendering graphics images. For instance, if an initial horizontal scaling parameter value for an object to be rendered is 0.2, GPU 32 may add the parameter modification value of −0.6 to the initial parameter value of 0.2, resulting in a parameter value of −0.4. GPU 32 may then use the resulting parameter value of −0.4 during rendering of the object.

While described with respect to a horizontal scaling parameter, the process described in the example of FIG. 8 may be performed similarly for various other parameter values as described herein. For instance, the process may be performed for a vertical scaling parameter, an overall scaling parameter, a vertical and/or horizontal translation parameter, rotation parameters, and other parameters. In some examples, computing device 2 may first determine parameters relating to shape aspects of the graphics image. Computing device 2 may next determine focus of the objects based on subsequent user feedback. In some examples, such as examples in which computing device 2 includes multiple displays, (e.g., stereo displays) computing device 2 may also determine parameters relating to the perceived depth aspects resulting from displayed graphics images. For instance, computing device 2 may render and display various stereo versions of a graphics image until the user indicates that objects in the graphics images properly appear three dimensional.

Figure 9:
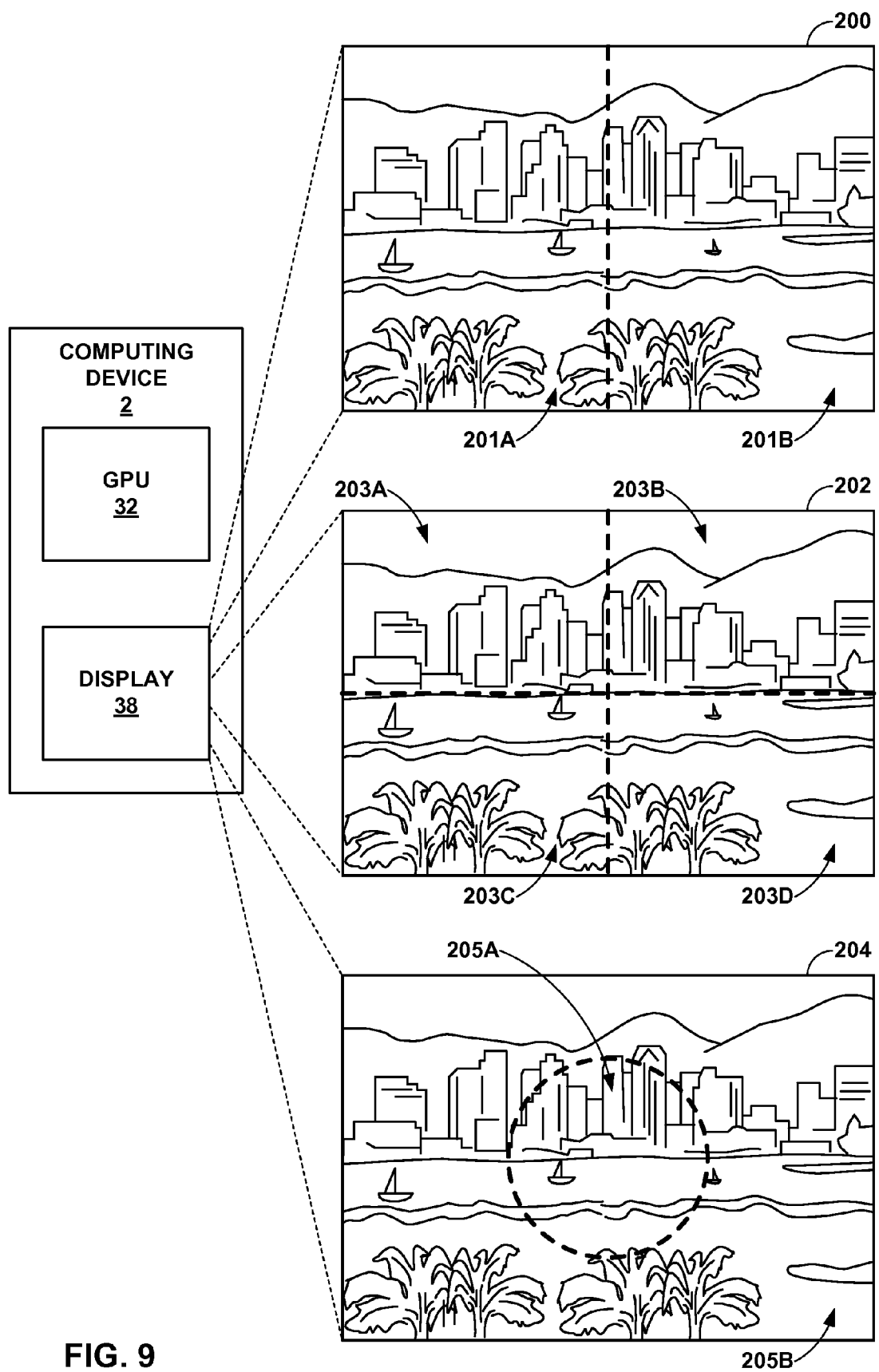
FIG. 9 is a block diagram illustrating an example computing device and graphics images for obtaining information indicative of user eyesight imperfections in accordance with the techniques of the present disclosure.

FIG. 9 is a block diagram illustrating an example computing device 2 and graphics images for obtaining information indicative of user eyesight imperfections in accordance with the techniques of the present disclosure. For purposes of illustration only, the example of FIG. 9 is described below within the context of FIGS. 1-3.

Computing device 2, as shown in the example of FIG. 9, may be configured to output graphics images, such as graphics images 200, 202, and 204, in order to obtain feedback indicative of a user's eyesight imperfections and/or correct for the user's eyesight imperfections. In some examples, a user's eyesight imperfections may not be uniform. That is, a user may have various eyesight issues that cause vision distortion in some areas of the user's view more than in other areas. In order to compensate for such imperfections, the techniques of the present disclosure may be applied to various portions of a display in a non-uniform manner, thereby providing stronger and/or different correction where needed without over-correcting in other areas.

Graphics image 200 provides one example of a corrected graphics image having different regions 201A and 201B. In the example of FIG. 9, GPU 32 may render region 201A based on a first set of one or more parameter values, and region 201B based on a second set of one or more parameter values. In various instances, one or both of the sets of parameter values may include parameter values based on parameter modification values determined using the techniques described herein. For instance, region 201A may be rendered using a first blurring parameter value, while region 201B is rendered using a second blurring parameter value.

Graphics image 202 provides another example of a corrected graphics image having different regions 203A-203D. In the example of FIG. 9, GPU 32 may render each of regions 203A-203D using different sets of parameter values. Graphics image 204 provides a third example of a corrected graphics image having different regions 205A and 205B. GPU 32 may render region 205A using a different set of parameter values than those used in rendering region 205B.

The techniques of the present disclosure may be used to render graphics images using different parameter values for any number of regions, having any size or shape. For instance, different parameter modification values may be determined and applied for each of a large number of concentric ringed regions. As another example, different parameter modification values may be determined and applied for numerous different square regions in a single image. Various other shapes and sizes of regions may be used in accordance with the techniques described herein.

Figure 10:
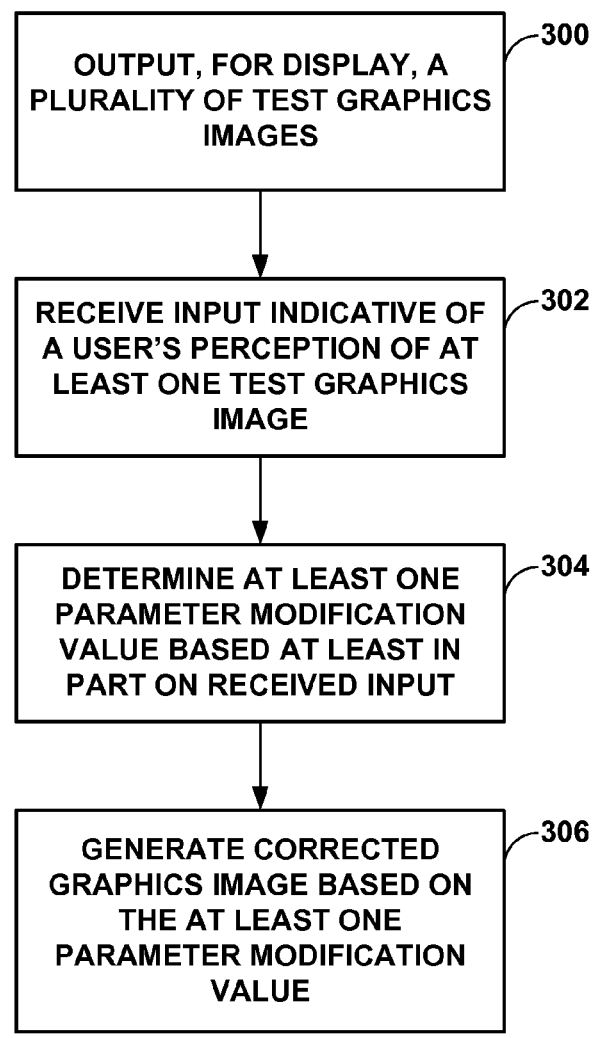
FIG. 10 is a flow diagram illustrating example operations of a computing device configured to implement the techniques of the present disclosure.

FIG. 10 is a flow diagram illustrating example operations of a computing device configured to implement the techniques of the present disclosure. For purposes of illustration only, the example operations of FIG. 10 are described below within the context of FIGS. 1-3.

In the example of FIG. 10, computing device 2 may output, for display, a plurality of test graphics images. Each test graphics image from the plurality may be generated (e.g., by GPU 32) based on a respective set of one or more parameter test values. For instance, GPU 32 may generate a first test graphics image based on a first set of parameter test values, generate a second test graphics image based on a second set of parameter test values, and so on. In some examples, each of the plurality of test graphics images may be output for display by computing device 2 in succession while in other examples, two or more of the plurality of test graphics images may be output for display concurrently.

Computing device 2, in the example of FIG. 10, may receive input indicative of a user's perception of at least one test graphics image (302). For instance, computing device 2 may receive a button press or voice input when the particular test graphics image is displayed, may receive input indicating the particular test graphics image (e.g., when more than one test graphics image is displayed concurrently), or receive other input indicative of the user's perception of at least one test graphics image. In some examples, computing device 2 may receive a single input. In other examples, computing device 2 may receive more than one input.

In the example of FIG. 10, computing device 2 may determine at least one parameter modification value based at least in part on the received input (304). For instance, when a single input associated with a single particular test graphics image is received, computing device 2 may determine parameter modification values to be the same as the parameter test values associated with the particular test graphics image. When multiple inputs are received (e.g., associated with multiple test graphics images), computing device 2 may determine parameter modification values by averaging the parameter test values associated with the multiple test graphics images or based on the parameter test values associated with the multiple test graphics images in some other way.

Computing device 2, in the example of FIG. 10, may generate a corrected graphics image based on the at least one parameter modification value (306). In some examples, computing device 2 (e.g., GPU 32) may render the corrected graphics image using a modified transformation matrix that is determined based on the at least one parameter modification value. In some examples, computing device 2 (e.g., GPU 32) may additionally or alternatively post process a rendered graphics image using a parameter value determined based on the at least one parameter modification value to generate the corrected graphics image.

In one or more examples, the functions described above may be implemented in hardware, software, firmware, or any combination thereof. If implemented in software, the functions may be stored as one or more instructions or code on an article of manufacture comprising a non-transitory computer-readable medium. Computer-readable media may include computer data storage media. Data storage media may be any available media that can be accessed by one or more computers or one or more processors to retrieve instructions, code and/or data structures for implementation of the techniques described in this disclosure. By way of example, and not limitation, such computer-readable media can comprise RAM, ROM, EEPROM, CD-ROM or other optical disk storage, magnetic disk storage, or other magnetic storage devices, flash memory, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

The code may be executed by one or more processors, such as one or more DSPs, general purpose microprocessors, ASICs, FPGAs, or other equivalent integrated or discrete logic circuitry. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a codec hardware unit or provided by a collection of interoperative hardware units, including one or more processors as described above, in conjunction with suitable software and/or firmware.

Various examples have been described. These and other examples are within the scope of the following claims.

What is claimed is:

1. A method of graphics processing comprising:
   outputting for display, by a computing device, a plurality of test graphics images;
   receiving, by the computing device, input indicative of a perception of how in focus a user of the computing device perceives at least one test graphics image from the plurality of test graphics images;
   determining, by the computing device and based at least in part on the received input, at least one parameter modification value; and
   generating, during graphics processing by the computing device, a corrected graphics image based at least in part on the at least one parameter modification value, wherein generating the corrected graphics image during graphics processing comprises:
   rendering the corrected graphics image by applying a modified transformation matrix to adjust the focus of the corrected graphics image during graphics processing using at least one of: a vertex shader, a pixel shader, or a fragment shader, the modified transformation matrix being determined based at least in part on the at least one parameter modification value, wherein:
   the at least one parameter modification value comprises a plurality of parameter modification values, including:
   a first parameter modification value from the plurality of parameter modification values corresponding to a first eye of a user of the computing device; and
   a second parameter modification value from the plurality of parameter modification values corresponding to a second eye of the user, the second eye being different from the first eye.

2. The method of claim 1, wherein outputting the plurality of test graphics images comprises outputting test graphics images that comprise a plurality of test objects.

3. The method of claim 2, wherein receiving the input indicative of the perception of the user of the at least one test graphics image further comprises receiving input indicating how centered the user perceives the plurality of test objects to be.

4. The method of claim 2, wherein receiving the input indicative of the perception of the user of the at least one test graphics image further comprises receiving input indicating how proportioned the user perceives the plurality of test objects to be.

5. The method of claim 2, wherein the plurality of test objects comprises a plurality of concentric circle objects.

6. The method of claim 1, wherein the at least one parameter modification value comprises at least one of a multiplication coefficient or an addition constant.

7. The method of claim 1, wherein:
   receiving the input indicative of the perception of how in focus the user of the computing device perceives at least one test graphics image comprises:
   receiving first input indicative of a perception of the user of a first region displaying the at least one test graphics image, and
   receiving second input indicative of a perception of the user of a second region displaying the at least one test graphics image;
   determining the at least one parameter modification value comprises:
   determining at least one first parameter modification value that corresponds to the first region, and
   determining at least one second parameter modification value that corresponds to the second region; and
   generating the corrected graphics image comprises:
   generating a first portion of the corrected graphics image based at least in part on the at least one first parameter modification value, the first portion of the corrected graphics image corresponding to the first region, and
   generating a second portion of the corrected graphics image based at least in part on the at least one second parameter modification value, the second portion of the corrected graphics image corresponding to the second region.

8. The method of claim 1, wherein generating the corrected graphics image comprises post processing a rendered graphics image using a parameter value determined based at least in part on the at least one parameter modification value to generate the corrected graphics image.

9. The method of claim 8, wherein post processing the rendered graphics image comprises:
   post processing the rendered graphics image using at least one of: a pixel shader, or a fragment shader to apply at least one of a blurring filter or a deconvolution filter to the rendered graphics image.

10. The method claim 1, wherein the modified transformation matrix comprises at least one of: a modified Model matrix, a modified View matrix, or a modified Projection matrix.

11. The method of claim 1 wherein the at least one parameter modification value comprises at least one of: a translation parameter modification value, a rotation parameter modification value, or a scaling parameter modification value.

12. An apparatus configured for graphics processing comprising:
   a memory configured to store graphics data; and
   one or more processors in communication with the memory, the one or more processors configured to:
   output, for display, a plurality of test graphics images;
   receive input indicative of a perception of how in focus a user of the computing device perceives at least one test graphics image from the plurality of test graphics images;
   determine, based at least in part on the received input, at least one parameter modification value; and
   generate, during graphics processing, a corrected graphics image based at least in part on the at least one parameter modification value, wherein the one or more processors are further configured to:
   render the corrected graphics image by applying a modified transformation matrix to adjust the focus of the corrected graphics image during graphics processing using at least one of: a vertex shader, a pixel shader, or a fragment shader, the modified transformation matrix being determined based at least in part on the at least one parameter modification value, wherein:

the at least one parameter modification value comprises a plurality of parameter modification values, including:

a first parameter modification value from the plurality of parameter modification values corresponding to a first eye of a user of the computing device; and a second parameter modification value from the plurality of parameter modification values corresponding to a second eye of the user, the second eye being different from the first eye.

13. The apparatus of claim 12, wherein the one or more processors are further configured to output test graphics images that comprise a plurality of test objects.

14. The apparatus of claim 13, wherein the one or more processors are further configured to receive input indicating how centered the user perceives the plurality of test objects to be.

15. The apparatus of claim 13, wherein the one or more processors are further configured to receive input indicating how proportioned the user perceives the plurality of test objects to be.

16. The apparatus of claim 13, wherein the plurality of test objects comprises a plurality of concentric circle objects.

17. The apparatus of claim 12, wherein the at least one parameter modification value comprises at least one of a multiplication coefficient or an addition constant.

18. The apparatus of claim 12, wherein the one or more processors are further configured to:

receive first input indicative of a perception of the user of a first region displaying the at least one test graphics image;

receive second input indicative of a perception of the user of a second region displaying the at least one test graphics image;

determine at least one first parameter modification value that corresponds to the first region;

determine at least one second parameter modification value that corresponds to the second region;

generate a first portion of the corrected graphics image based at least in part on the at least one first parameter modification value, the first portion of the corrected graphics image corresponding to the first region; and generate a second portion of the corrected graphics image based at least in part on the at least one second parameter modification value, the second portion of the corrected graphics image corresponding to the second region.

19. The apparatus of claim 12, wherein the one or more processors are further configured to:

post process a rendered graphics image using a parameter value determined based at least in part on the at least one parameter modification value to generate the corrected graphics image.

20. The apparatus of claim 19, wherein the one or more processors are further configured to:

post process the rendered graphics image using at least one of: a pixel shader, or a fragment shader to apply at least one of a blurring filter or a deconvolution filter to the rendered graphics image.

21. The apparatus of claim 12, wherein the modified transformation matrix comprises at least one of: a modified Model matrix, a modified View matrix, or a modified Projection matrix.

22. The apparatus of claim 12, wherein the at least one parameter modification value comprises at least one of: a translation parameter modification value, a rotation parameter modification value, or a scaling parameter modification value.

23. A non-transitory computer-readable storage medium storing instructions that, when executed, cause one or more processors of a device configured for graphics processing to:

output, for display, a plurality of test graphics images;

receive input indicative of a perception of how in focus a user of the computing device ef perceives at least one test graphics image from the plurality of test graphics images;

determine, based at least in part on the received input, at least one user parameter modification value; and generate, during graphics processing, a corrected graphics image based at least in part on the at least one user parameter modification value, wherein the instructions further cause the one or more processors to:

render the corrected graphics image by applying a modified transformation matrix to adjust the focus of the corrected graphics image during graphics processing using at least one of: a vertex shader, a pixel shader, or a fragment shader, the modified transformation matrix being determined based at least in part on the at least one user parameter modification value, wherein:

the at least one parameter modification value comprises a plurality of parameter modification values, including:

a first parameter modification value from the plurality of parameter modification values corresponding to a first eye of a user of the computing device; and a second parameter modification value from the plurality of parameter modification values corresponding to a second eye of the user, the second eye being different from the first eye.

24. An apparatus configured to process graphics, the apparatus comprising:

means for outputting, for display, a plurality of test graphics images;

means for receiving input indicative of a perception of how in focus a user of the computing device perceives at least one test graphics image from the plurality of test graphics images;

means for determining, based at least in part on the received input, at least one parameter modification value; and means for generating, during graphics processing, a corrected graphics image based at least in part on the at least one parameter modification value, wherein the means for generating the corrected graphics image further comprises:

means for rendering the corrected graphics image by applying a modified transformation matrix to adjust the focus of the corrected graphics image during graphics processing using at least one of: a vertex shader, a pixel shader, or a fragment shader, the modified transformation matrix being determined based at least in part on the at least one parameter modification value, wherein:

the at least one parameter modification value comprises a plurality of parameter modification values, including a first parameter modification value from the plurality of parameter modification values corresponding to a first eye of a user of the computing device; and a second parameter modification value from the plurality of parameter modification values corresponding to a second eye of the user, the second eye being different from the first eye.

* * * * *